United States Patent
Hirai et al.

(10) Patent No.: US 8,232,051 B2
(45) Date of Patent: Jul. 31, 2012

(54) PRIMER SET FOR GENE AMPLIFICATION, REAGENT FOR GENE AMPLIFICATION INCLUDING THE SAME, AND USES THEREOF

(75) Inventors: Mitsuharu Hirai, Kyoto (JP); Satoshi Majima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 551 days.

(21) Appl. No.: 12/306,370

(22) PCT Filed: Mar. 24, 2008

(86) PCT No.: PCT/JP2008/055469
§ 371 (c)(1),
(2), (4) Date: Dec. 23, 2008

(87) PCT Pub. No.: WO2008/117782
PCT Pub. Date: Oct. 2, 2008

(65) Prior Publication Data
US 2009/0233288 A1 Sep. 17, 2009

(30) Foreign Application Priority Data
Mar. 26, 2007 (JP) ................................. 2007-079403

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.1; 435/91.1; 435/91.2; 536/23.1; 536/24.3

(58) Field of Classification Search ........................ None
See application file for complete search history.

(56) References Cited

FOREIGN PATENT DOCUMENTS
WO    WO 99/15704    * 4/1999

OTHER PUBLICATIONS

Bodin et al; Blood, vol. 106, pp. 135-140; 2005.*
Hoorfar et al; J Clin Microbiology, vol. 42, pp. 1863-1868, 2004.*
Office Action issued in Korean Application No. 10-2008-7025612 dated Dec. 14, 2010. (Partial translation of Notification of Reasons for Refusal included).
Sconce et al., "The impact of CYP2C9 and VKORC1 genetic polymorphism and patient characteristics upon warfarin dose requirements: proposal for a new dosing regimen," Blood, 2005, 106(7), pp. 2329-2333.
Mushiroda et al, "Association of *VKORC1* and *CYP2C9* polymorphisms with warfarin dose requirements in Japanese patients," Journal of Human Genetics, vol. 51, No. 3, pp. 249-253, 2006.
International Search Report of PCT/JP2008/055469, dated May 13, 2008.
Rost et al. "Mutations in *VKORC1* cause warfarin resistance and multiple coagulation factor deficiency type 2." Nature—Letters to Nature, vol. 427, Feb. 5, 2004, pp. 537-455.
Rieder et al. "Effect of *VKORC1* Hyplotypes on Transcriptional Regulation and Warfarin Dose," The New England Journal of Medicine, vol. 352(22), Jun. 2, 2005, pp. 2285-2293.
Takahashi. "Genetic testing related to the individual difference of warfarin dosage." Kensa to Gijutsu, vol. 34(10), Oct. 1, 2006, pp. 984-986.

* cited by examiner

*Primary Examiner* — Jehanne Sitton
(74) *Attorney, Agent, or Firm* — Morgan, Lewis & Bockius LLP

(57) ABSTRACT

Primer sets for amplifying two genes (the CYP2C9 gene and the VKORC1 gene) by a gene amplification method are provided, wherein the primer sets can amplify respective target regions of the two genes specifically and efficiently in the same reaction system simultaneously. Two pairs of primer sets are used including forward primers consisting of the base sequences of SEQ ID NOs: 5 and 29 as well as reverse primers consisting of the base sequences of SEQ ID NOs: 18 and 38, respectively. The use of these primer sets makes it possible to specifically amplify target regions including sites where polymorphisms to be detected are generated in the CYP2C9 gene and the VKORC1 gene, in the same reaction solution simultaneously.

15 Claims, 5 Drawing Sheets

VKORC1 6484 T/C
CYP2C9 *1/*1

VKORC1

CYP2C9

PRIMER SET FOR GENE AMPLIFICATION, REAGENT FOR GENE AMPLIFICATION INCLUDING THE SAME, AND USES THEREOF

TECHNICAL FIELD

The present invention relates to primer sets for simultaneously amplifying the CYP2C9 gene and the VKORC1 gene, reagents for gene amplification including the same, and uses thereof.

BACKGROUND ART

With respect to patients with myocardial infarction or cerebral infarction, warfarin is used widely as a drug for preventing blood coagulation. The suitable dose of warfarin differs considerably depending on the race and further there are differences among individuals even though they are of the same race. When a large amount of warfarin is administered, there is a risk of causing, for example, epistaxis or internal hemorrhage in the skin as well as side effects such as intracerebral hemorrhage in some cases. Accordingly, it is very important to determine the suitable dose of warfarin for each patient individually in the treatment.

In determining such a suitable dose value of warfarin, recently, it has been reported that polymorphisms of the CYP2C9 gene and the VKORC1 gene are associated with the drug action of warfarin (Nonpatent Document 1 and Nonpatent Document 2). The CYP2C9 gene is a gene that codes for cytochrome P450, which produces a warfarin metabolic enzyme. The VKORC1 gene is a gene that codes for protein, which acts on vitamin K involved in blood coagulation. Therefore to detect polymorphisms of these two genes also is very important for determining the suitable dose of warfarin for each patient to reduce the side effects.

On the other hand, detection of a point mutation, a so-called single nucleotide polymorphism (SNP), is performed widely as a method of analyzing, at the gene level, for example, the causes of all types of diseases and the individual differences in disease liability (susceptibility to diseases) and in drug action. Examples of common methods of detecting a point mutation include: (1) a direct sequencing method in which the region corresponding to a sequence to be subjected to detection in a target DNA of a sample is amplified by polymerase chain reaction (PCR) and all the gene sequences thereof are analyzed, (2) RFLP analysis in which the region corresponding to a sequence to be subjected to detection in a target DNA of a sample is amplified by PCR, the amplification product thus obtained is cut with a restriction enzyme whose cleaving action differs depending on the presence or absence of the target mutation in the sequence to be subjected to detection and is then electrophoresed, and thereby typing is performed, and (3) an ASP-PCR method in which PCR is performed using a primer with a target mutation located in the 3'-end region and the mutation is judged depending on the presence or absence of amplification.

However, since these methods require, for example, purification of DNA extracted from a sample, electrophoresis, and a treatment with a restriction enzyme, they take time and cost. Furthermore, after PCR is performed, it is necessary to open the reaction container once. Accordingly, there is a possibility that the amplification product may contaminate the next reaction system and thereby the analysis accuracy may be deteriorated. Moreover, since it is difficult to automate, multiple samples cannot be analyzed. Further, the aforementioned ASP-PCR method (3) has lower specificity, which also is a problem.

Because of these problems, recently, a method of analyzing the melting temperature (Tm) of double-stranded nucleic acid formed of a probe and target nucleic acid is used as a method of detecting a point mutation. Since such a method is performed through, for example, Tm analysis or analysis of the melting curve of a double strand, it is referred to as melting curve analysis. This method is described below. That is, first, a probe complementary to a sequence to be subjected to detection containing a point mutation to be detected is used to form a hybrid (double-stranded DNA) between the aforementioned probe and a target single-stranded DNA contained in a detection sample. Subsequently, this hybridization product is heat-treated, and dissociation (melting) of the hybrid accompanying the temperature rise is detected by a change in a signal of, for example, absorbance. The Tm value then is determined based on the result of the detection and the presence or absence of any point mutation is judged accordingly. The higher the homology of the hybridization product, the higher the Tm value, and the lower the homology, the lower the Tm value. Therefore the Tm value (reference value for assessment) is determined beforehand with respect to the hybridization product between the sequence to be subjected to detection containing a point mutation and a probe complementary thereto, and then the Tm value (measured value) of the hybridization product between the target single-stranded DNA contained in the detection sample and the aforementioned probe is measured. When the measured value is comparable to the reference value, it is considered as matching, that is, it can be judged that a point mutation is present in the target DNA. On the other hand, when the measured value is lower than the reference value, it is considered as mismatching, that is, it can be judged that no point mutation is present in the target DNA. Furthermore, according to this method, it also is possible to automate gene analysis.

However, such a detection method using Tm analysis also has a problem in that plural sequences cannot be analyzed in one reaction solution as in the cases of the aforementioned analysis methods (1) to (3). As described above, a polymorphism of the CYP2C9 gene and a polymorphism of the VKORC1 gene are associated with the effect of warfarin. Accordingly, it is desirable to analyze the polymorphisms of both the genes and to determine comprehensively the prescription of warfarin based on the results of the analyses. However, since isozymes are present in the respective genes, there is a possibility that genes coding for isozymes other than the target genes also are amplified in PCR. In conventional methods, therefore, for example, in order to check the respective polymorphisms of the CYP2C9 gene and the VKORC1 gene, it was necessary to amplify target regions of the respective genes in different reaction systems, respectively, and to analyze the resultant amplification products separately. As described above, in conventional methods, it is very difficult to allow only these two genes to serve as templates and to amplify specifically only the respective target regions of the respective genes. Furthermore, as described above, since even the analysis of one sample is accompanied by a considerable amount of time and energy, it is not practical to analyze multiple samples, which is a problem.

[Nonpatent Document 1] Simone Rost et al., Nature Vol. 427 2004 letters to nature

[Nonpatent Document 2] Mark J. Rieder et al., The New England Journal of Medicine 352; 22, 2005

DISCLOSURE OF INVENTION

Hence, the present invention is intended to provide a primer set for amplifying two types of genes (the CYP2C9 and VKORC1 genes) by a gene amplification method, wherein the respective target regions of the two types of genes can be amplified specifically and efficiently in the same reaction system simultaneously.

In order to achieve the aforementioned object, a primer set of the present invention is a primer set for amplifying two types of genes simultaneously by a gene amplification method, wherein the two types of genes are the CYP2C9 gene and the VKORC1 gene, and the primer set includes the following two types of primer sets (1) and (2):

Primer Set (1):

a primer set of a pair of primers including a forward primer composed of the following oligonucleotide (F1) and a reverse primer composed of the following oligonucleotide (R1):
(F1): at least one oligonucleotide having a sequence identical to that of a region extending from adenine (A) at base 466 to be considered as the first base to any one of the $14^{th}$ to $18^{th}$ bases in the direction toward the 5' end in the base sequence of SEQ ID NO: 1, with the adenine (A) being the 3' end, and
(R1): at least one oligonucleotide complementary to a region extending from thymine (T) at base 631 to be considered as the first base to any one of the $19^{th}$ to $36^{th}$ bases in the direction toward the 3' end in the base sequence of SEQ ID NO: 1, with adenine (A) complementary to the thymine (T) at base 631 being the 3' end, and Primer Set (2):

a primer set of a pair of primers including a forward primer composed of the following oligonucleotide (F2) and a reverse primer composed of the following oligonucleotide (R2):
(F2): at least one oligonucleotide having a sequence identical to that of a region extending from adenine (A) at base 440 to be considered as the first base to any one of the $21^{st}$ to $27^{th}$ bases in the direction toward the 5' end in the base sequence of SEQ ID NO: 2, with the adenine (A) being the 3' end, and
(R2): at least one oligonucleotide complementary to a region extending from adenine (A) at base 541 to be considered as the first base to any one of the $18^{th}$ to $25^{th}$ bases in the direction toward the 3' end in the base sequence of SEQ ID NO: 2, with thymine (T) complementary to the adenine (A) at base 541 being the 3' end.

A reagent for gene amplification of the present invention is a reagent for amplifying two types of genes by a gene amplification method, wherein the two types of genes are the CYP2C9 gene and the VKORC1 gene, and the reagent includes the primer set for gene amplification of the present invention.

A process for producing amplification products of the present invention is a process for producing amplification products of two types of genes by a gene amplification method, wherein the two types of genes are the CYP2C9 gene and the VKORC1 gene, and the process includes the following step (I):

(I) amplifying the CYP2C9 gene and the VKORC1 gene simultaneously in the same reaction solution using a primer set for gene amplification of the present invention, with nucleic acid contained in a sample being used as a template.

A polymorphism analysis method of the present invention is a method of analyzing polymorphisms of sites to be detected in genes, wherein the genes are the CYP2C9 gene and the VKORC1 gene, and the method includes the following steps (i) to (iv):

(i) simultaneously amplifying a region including a site to be detected in the CYP2C9 gene and a region including a site to be detected in the VKORC1 gene in the same reaction solution by a process for producing amplification products of the present invention, (ii) preparing a reaction solution that contains the amplification product of the CYP2C9 gene and the amplification product of the VKORC1 gene obtained in step (i) as well as probes capable of hybridizing to the respective sites to be detected in the respective genes, (iii) measuring signal values that indicate melting states of the respective hybridization products between the respective amplification products and the respective probes while changing the temperature of the reaction solution, and (iv) determining polymorphisms of the respective sites to be detected from a change in the signal values accompanying a change in the temperature.

The primer set of the present invention makes it possible simultaneously and specifically to amplify respective target regions (regions including sites where the polymorphisms to be detected are present) of the CYP2C9 gene and the VKORC1 gene in the same reaction solution. Accordingly, the time and cost for amplifying target regions can be reduced, which is different from the conventional methods described above. Furthermore, as described above, since the respective target regions of the two types of genes are amplified specifically in the same reaction solution, for example, the use of probes complementary to sequences to be subjected to detection in the respective target regions makes it possible to perform Tm analysis by directly using the reaction solution to type the polymorphisms of the respective genes. Moreover, since amplification and typing can be performed with one reaction solution, it also is possible to automate the operation. Furthermore, since the use of the primer set of the present invention allows a pretreatment to be omitted even in the case of, for example, a contaminated sample (for instance, whole blood or oral mucosa), the amplification reaction can be carried out quicker and more easily. Moreover, since the use of the primer set of the present invention allows the amplification reactions to be carried out with higher amplification efficiency as compared to conventional cases, the amplification reaction time also can be shortened. Thus, according to the primer set of the present invention and the reagent including the same as well as the process for producing amplification products using them, since respective polymorphisms in the CYP2C9 gene and the VKORC1 gene can be analyzed quickly and easily, the present invention can be said to be very effective in the medical field.

BEST MODE FOR CARRYING OUT THE INVENTION

Primer Set for Gene Amplification

Figure 1:
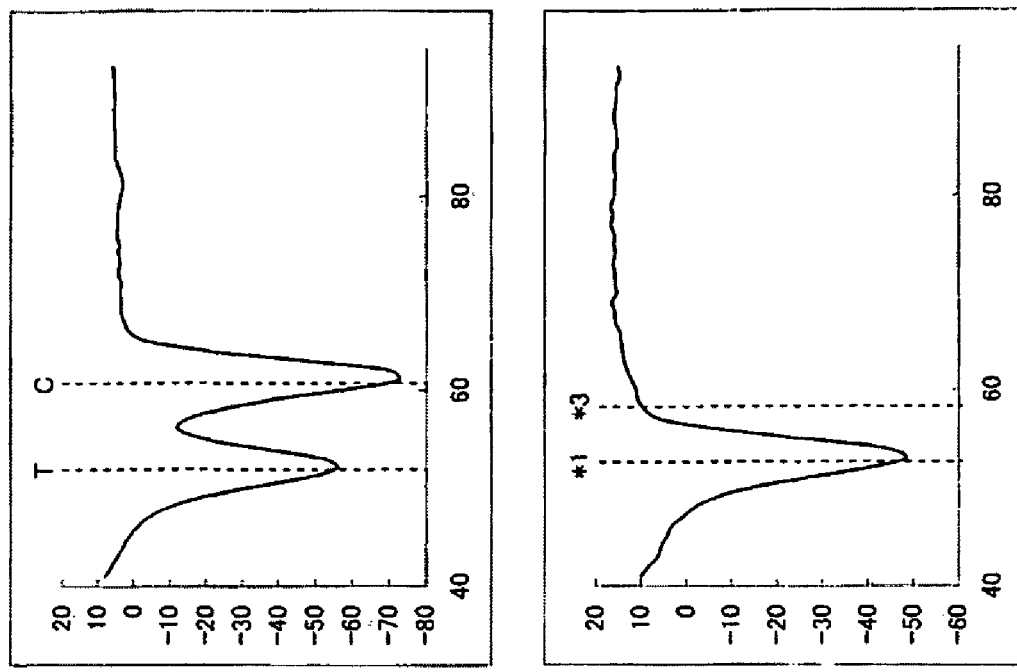
FIG. 1 shows graphs indicating the results of Tm analysis in an example of the present invention.
Figure 1:
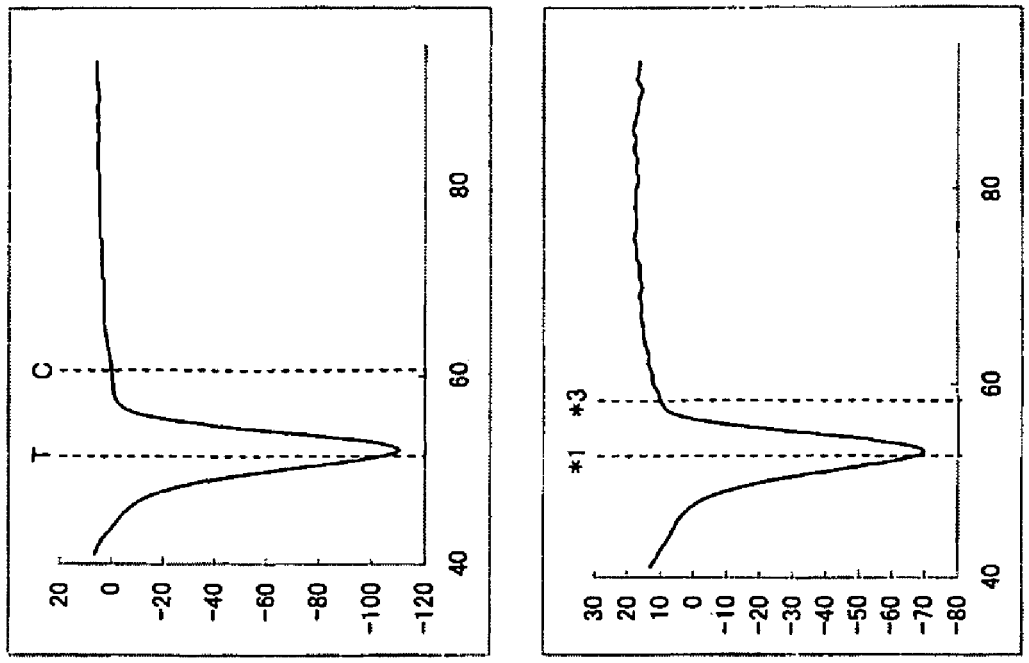

As described above, the primer set for gene amplification of the present invention is characterized by including the two types of primer sets (1) and (2). The regions to be amplified with the primer set of the present invention are a region including a site (at base 521 in SEQ ID NO: 1) where a polymorphism is to be detected in the case of the CYP2C9 gene and a region including a site (at base 484 in SEQ ID NO: 2) where a polymorphism is to be detected in the case of the VKORC1 gene, which are described later. Accordingly, when the target regions of the respective genes are amplified using the primer set of the present invention, the polymorphisms of the two types of genes can be analyzed more efficiently as compared to conventional cases. Hereinafter, the "forward primer" also may be referred to as an "F primer" and the "reverse primer" as an "R primer".

First, the primer set (1) for amplifying the CYP2C9 gene is described. As described above, the primer set (1) is a primer set of a pair of primers including a forward primer composed of the following oligonucleotide (F1) and a reverse primer composed of the following oligonucleotide (R1) (hereinafter also referred to as a "primer set for the CYP2C9 gene"):
(F1): at least one oligonucleotide having a sequence identical to that of a region extending from adenine (A) at base 466 to be considered as the first base to any one of the $14^{th}$ to $18^{th}$ bases in the direction toward the 5' end in the base sequence of SEQ ID NO: 1, with the adenine (being the 3' end, and
(R1): at least one oligonucleotide complementary to a region extending from thymine (T) at base 631 to be considered as the first base to any one of the $19^{th}$ to $36^{th}$ bases in the direction toward the 3' end in the base sequence of SEQ ID NO: 1, with adenine (A) complementary to the thymine (T) at base 631 being the 3' end.

The base sequence indicated in SEQ ID NO: 1 is a partial sequence of the full-length sequence of the Homo sapiens cytochrome P450 family 2 subfamily C polypeptide 9 (CYP2C9). Specifically, the aforementioned base sequence corresponds to, for example, a region between 52,001 and 53,000 in the full-length sequence of the CYP2C9 that has been registered at NCBI under accession No. AY702706.

The primer set for the CYP2C9 gene is a primer set for amplifying a DNA strand including a region between base 467 and base 630 in SEQ ID NO: 1 and a strand complementary thereto. In this region, base 521 (i.e. base 521 in SEQ ID NO: 1) and base 522 (i.e. base 522 in SEQ ID NO: 1) are known for the presence of point mutations (A521C, T522C) that affect the function of the CYP2C9.

The 521C polymorphism is referred to as "CYP2C9*3", while the wildtype sequence generally is referred to as "CYP2C9*1". The 521C polymorphism indicates a polymorphism in which amino acid 359 is isoleucine (Ile) when base 521 is A and amino acid 359 is leucine (Leu) when base 521 is C, in the case where the CYP2C9 gene is translated into protein. In the present invention, the polymorphism of this site can be indicated as CYP2C9*1/*1 (521A/A) or CYP2C9*3/*3 (521C/C) in the case of a homozygote and as CYP2C9*1/*3 (521A/C) in the case of a heterozygote. Furthermore, the 522C polymorphism is referred to as "CYP2C9*4", while the wildtype sequence generally is referred to as "CYP2C9*1". The 522C polymorphism indicates a polymorphism in which amino acid 359 is isoleucine (Ile) when base 522 is T and amino acid 359 is threonine (Thr) when base 522 is C, in the case where the CYP2C9 gene is translated into protein. In the present invention, the polymorphism of this site can be indicated as CYP2C9*1/*1 (522T/T) or CYP2C9*4/*4 (522C/C) in the case of a homozygote and as CYP2C9*1/*4 (522T/C) in the case of a heterozygote. Hereinafter, this primer set (1) also may be referred to as a "primer set for CYP2C9".

In the present invention, the F1 primer and R1 primer of the primer set (1) can be any primers, as long as the base located at the 3' end that serves to determine the site from which DNA polymerase starts amplification satisfies the aforementioned condition. Fixation of the base located at the 3' end of each primer in this manner makes it possible sufficiently to prevent the primer set (1) from being bound to, for example, another similar isozyme gene (for example, the CYP2C8, CYP2C17, CYP2C18, or CYP2C19 gene).

As described above, since the F1 primer and R1 primer each can be any primer as long as the base located at the 3' end is fixed, the length itself of each primer is not particularly limited and can be adjusted suitably to a common length. The length of the primers is, for example, in the range of 13- to 50-mers, preferably 14- to 45-mers, and more preferably 15- to 40-mers. Specifically, it is preferable that the F1 primer be at least one oligonucleotide having a sequence identical to that of a region extending from adenine (A) at base 466 to be considered as the first base to any one of the $14^{th}$ to $18^{th}$ bases (preferably the $14^{th}$ to $17^{th}$ bases and more preferably the $15^{th}$ to $17^{th}$ bases) in the direction toward the 5' end in the base sequence of SEQ ID NO: 1. Furthermore, it is preferable that the R1 primer be at least one oligonucleotide complementary to a region extending from thymine (T) at base 631 to be considered as the first base to any one of the $19^{th}$ to $36^{th}$ bases (preferably the $22^{nd}$ to $30^{th}$ bases and more preferably the $23^{rd}$ to $29^{th}$ bases) in the direction toward the 3' end in the base sequence of SEQ ID NO: 1. Since each 3' end of the F1 primer and the R1 primer is fixed, the region to be elongated from the primer is, for example, a region between base 467 and base 630 in SEQ ID NO: 1 as described above. However, the length of the whole resultant amplification product varies according to the length of the primer to be used.

Furthermore, it is not necessary for the R1 primer and the F1 primer to be oligonucleotides perfectly complementary to the base sequence indicated in SEQ ID NO: 1 and to that of the strand complementary to the aforementioned base sequence, respectively. In other words, the part excluding the base located at the 3' end in each primer may be different in one to five bases from that of a perfectly complementary oligonucleotide.

Specific examples of the F1 primer and the R1 primer are indicated below but the present invention is not limited thereto. The combination of these F1 primer and R1 primer is not limited by any means. Specifically, however, a primer set (1') is particularly preferable, which includes a F1' primer composed of oligonucleotide of SEQ ID NO: 5, and a R1' primer composed of oligonucleotide of SEQ ID NO: 18. "Tm (° C.)" indicated below in the table is Tm (° C.) obtained when each sequence indicated below in the table was hybridized with the sequence perfectly complementary thereto. The "Tm (° C.)" is a value calculated by using MELTCALC software (meltcalc.com/), with parameters including an oligonucleotide concentration of 0.2 µM and a sodium equivalent (Na eq.) of 50 mM (the same applies below). The Tm value can be calculated by using, for example, conventionally known MELTCALC software (meltcalc.com/) or also can be determined by the nearest neighbor method (the same applies below).

TABLE 1

| Primer | Sequence | Tm (° C.) | SEQ ID NO. |
|---|---|---|---|
| F Primer | 5'-cggagccctgcatgcaa-3' | 59.4 | 3 |
|  | 5'-ggagccctgcatgcaa-3' | 56.5 | 4 |
|  | 5'-gagccctgcatgcaa-3' | 53.6 | 5 |
|  | 5'-agccctgcatgcaa-3' | 52.1 | 6 |
|  | 5'-gccctgcatgcaa-3' | 50.2 | 7 |
| R Primer | 5'-gtttaaaaatgatactatgaatttggggacttcgaa-3' | 58.1 | 8 |
|  | 5'-tttaaaaatgatactatgaatttggggacttcgaa-3' | 57.5 | 9 |
|  | 5'-ttaaaaatgatactatgaatttggggacttcgaa-3' | 57.2 | 10 |
|  | 5'-taaaaatgatactatgaatttggggacttcgaa-3' | 56.9 | 11 |
|  | 5'-aaaaatgatactatgaatttggggacttcgaa-3' | 57.2 | 12 |
|  | 5'-aaaatgatactatgaatttggggacttcgaa-3' | 56.9 | 13 |
|  | 5'-aaatgatactatgaatttggggacttcgaa-3' | 56.6 | 14 |
|  | 5'-aatgatactatgaatttggggacttcgaa-3' | 56.3 | 15 |
|  | 5'-atgatactatgaatttggggacttcgaa-3' | 55.9 | 16 |
|  | 5'-tgatactatgaatttggggacttcgaa-3' | 55.7 | 17 |
|  | 5'-gatactatgaatttggggacttcgaa-3' | 54.5 | 18 |
|  | 5'-atactatgaatttggggacttcgaa-3' | 53.6 | 19 |
|  | 5'-tactatgaatttggggacttcgaa-3' | 53.3 | 20 |
|  | 5'-actatgaatttggggacttcgaa-3' | 53.5 | 21 |
|  | 5'-ctatgaatttggggacttcgaa-3' | 52 | 22 |
|  | 5'-tatgaatttggggacttcgaa-3' | 50.9 | 23 |
|  | 5'-atgaatttggggacttcgaa-3' | 51 | 24 |
|  | 5'-tgaatttggggacttcgaa-3' | 50.5 | 25 |

Next, the primer set (2) for amplifying the VKORC1 gene is described. As described above, the primer set (2) is a primer set of a pair of primers including a forward primer composed of the following oligonucleotide (F2) and a reverse primer composed of the following oligonucleotide (R2) (hereinafter, this primer set (2) also may be referred to as a "primer set for the VKORC1 gene")):
(F2): at least one oligonucleotide having a sequence identical to that of a region extending from adenine (A) at base 440 to be considered as the first base to any one of the $21^{st}$ to $27^{th}$ bases in the direction toward the 5' end in the base sequence of SEQ ID NO: 2, with the adenine (A) being the 3' end, and
(R2): at least one oligonucleotide complementary to a region extending from adenine (A) at base 541 to be considered as the first base to any one of the $18^{th}$ to $25^{th}$ bases in the direction toward the 3' end in the base sequence of SEQ ID NO: 2, with thymine (T) complementary to the adenine (A) at base 541 being the 3' end.

The base sequence indicated in SEQ ID NO: 2 is a partial sequence of the full-length sequence of the VKORC1 gene that codes for Homo sapiens vitamin K epoxide reductase complex, subunit 1 (VKORC1). Specifically, the aforementioned base sequence corresponds to a region between base 6001 and base 7000 in the full-length sequence of the VKORC1 gene that has been registered at NCBI under accession No. AY587020.

The primer set for the VKORC1 gene is a primer set for amplifying a DNA strand including a region between base 441 and base 540 in SEQ ID NO: 2 as well as a strand complementary thereto. Base 484 in this region (i.e. base 484 in SEQ ID NO: 2) is known for the presence of a point mutation (484C, 484T). These polymorphisms can be indicated as, for example, 484C/C or 484T/T in the case of a homozygote and as 484C/T in the case of a heterozygote. Furthermore, when those polymorphisms each are a homozygote, they can be indicated as, for example, 6484C/C, 6484T/T, or 6484C/T according to the number of the base in the full length (hereinafter, they are indicated in this manner). It has been reported that generally, the polymorphism of base 6484 often is C in the case of Europeans while being T in the case of Japanese.

For the same reason as that described with respect to the primer set for the CYP2C9 gene, the F2 primer and the R2 primer of the primer set for the VKORC1 gene can be any primers, as long as the base located at the 3' end that serves to determine the site from which DNA polymerase starts amplification satisfies the aforementioned condition. Accordingly, the length itself of the F2 primer and R2 primer is not particularly limited and can be, for example, the same length as that described above. Specifically, it is preferable that the F2 primer be at least one oligonucleotide having a sequence identical to that of a region extending from adenine (A) at base 440 to be considered as the first base to any one of the $21^{st}$ to $27^{th}$ bases (preferably the $22^{nd}$ to $26^{th}$ bases and more preferably the $23^{rd}$ to $25^{th}$ bases) in the direction toward the 5' end in the base sequence of SEQ ID NO: 2. Furthermore, it is preferable that the R2 primer be at least one oligonucleotide complementary to a region extending from adenine (A) at base 541 to be considered as the first base to any one of the $18^{th}$ to $25^{th}$ bases (preferably the $18^{th}$ to $23^{rd}$ bases and more preferably the $19^{th}$ to $22^{nd}$ bases) in the direction toward the 3' end in the base sequence of SEQ ID NO: 2. Since each 3' end of the F2 primer and the R2 primer is fixed, the region to be elongated from the primer is, for example, a region between base 441 and base 540 in SEQ ID NO: 2 as described above. However, the length of the whole resultant amplification product varies according to the length of the primer to be used.

Furthermore, it is not necessary for the R2 primer and the F2 primer to be oligonucleotides perfectly complementary to the base sequence indicated in SEQ ID NO: 2 and to that of the strand complementary to the aforementioned base sequence, respectively. In other words, the part excluding the base located at the 3' end in each primer may be different in one to five bases from that of a perfectly complementary oligonucleotide.

Specific examples of the F2 primer and the R2 primer are indicated below but the present invention is not limited thereto. The combination of these F2 primer and R2 primer is not limited by any means. Specifically, however, a primer set (2') is particularly preferable, which includes an F2' primer composed of oligonucleotide of SEQ ID NO: 29 and an R2' primer composed of oligonucleotide of SEQ ID NO: 38.

TABLE 2

| Primer | Sequence | Tm (° C.) | SEQ ID NO. |
|---|---|---|---|
| F Primer | 5'-ggggaggatagggtcagtgacatggaa-3' | 62.2 | 26 |
| | 5'-gggaggatagggtcagtgacatggaa-3' | 60.6 | 27 |
| | 5'-ggaggatagggtcagtgacatggaa-3' | 58.9 | 28 |
| | 5'-gaggatagggtcagtgacatggaa-3' | 57 | 29 |
| | 5'-aggatagggtcagtgacatggaa-3' | 56.2 | 30 |
| | 5'-ggatagggtcagtgacatggaa-3' | 55 | 31 |
| | 5'-gatagggtcagtgacatggaa-3' | 52.8 | 32 |
| R Primer | 5'-ttggaccctgcccgagaaaggtgat-3' | 63.2 | 33 |
| | 5'-tggaccctgcccgagaaaggtgat-3' | 63.1 | 34 |
| | 5'-ggaccctgcccgagaaaggtgat-3' | 62 | 35 |
| | 5'-gaccctgcccgagaaaggtgat-3' | 60.1 | 36 |
| | 5'-accctgcccgagaaaggtgat-3' | 59.4 | 37 |
| | 5'-ccctgcccgagaaaggtgat-3' | 57.9 | 38 |
| | 5'-cctgcccgagaaaggtgat-3' | 55.6 | 39 |
| | 5'-ctgcccgagaaaggtgat-3' | 53 | 40 |

For example, in order to shorten the reaction time, each primer of the aforementioned primer sets (1) and (2) can be one with any conventionally known sequence added to the 5' end.

Preferably, the primer sets for gene amplification of the present invention including such primer sets (1) and (2) are used in simultaneously amplifying the CYP2C9 gene and the VKORC1 gene in a biological sample such as a whole blood sample. Particularly, when they are used together with probes for detecting polymorphisms described later, it is preferable that they be used in the gene amplification method in which the ratio of whole blood sample to be added to a reaction solution for gene amplification is 0.1 to 0.5 vol %. This is described later.

<Reagent for Gene Amplification>

As described above, the reagent for gene amplification of the present invention is a reagent for amplifying two types of genes by a gene amplification method. It is characterized in that the two types of genes are the CYP2C9 gene and the VKORC1 gene, and the reagent includes a primer set for gene amplification of the present invention. The reagent for gene amplification of the present invention is characterized by including a primer set of the present invention and, for example, components other than this are not limited by any means.

For example, in order to detect an amplification product that is obtained by a gene amplification method using a primer set of the present invention, the reagent for gene amplification of the present invention further may include at least one of a probe that hybridizes to a site to be detected in the CYP2C9 gene and a probe that hybridizes to a site to be detected in the VKORC1 gene. Particularly, it is preferable that it include both the probes. As described above, the primer set of the present invention makes it possible to amplify specifically the respective target regions of the two types of genes (the CYP2C9 gene and the VKORC1 gene) by the gene amplification method. Accordingly, when two types of probes that are complementary to the sequences to be subjected to detection in the target regions of the CYP2C9 gene and the VKORC1 gene are allowed to coexist, for instance, the presence or absence of amplification of each target region or the polymorphism to be detected can be detected by the method described later. Such probes and the method of utilizing the same are described when the method of analyzing a polymorphism is described later. Preferably, the reagent for gene amplification of the present invention is used in amplifying the two types of genes in a biological sample such as whole blood. Particularly, when it is used together with the aforementioned probes, it is preferable that the reagent for gene amplification of the present invention be used in the gene amplification method in which the ratio of a whole blood sample to be added to a reaction solution for gene amplification is 0.1 to 0.5 vol %. In the present invention, the "sequence to be subjected to detection" denotes a sequence including a site where a polymorphism is present (a site to be detected).

The form of the reagent for gene amplification of the present invention is not particularly limited. For example, it may be a liquid reagent containing a primer set for gene amplification of the present invention or may be a dry reagent that is suspended in a solvent before use. Furthermore, the content of a primer set for gene amplification of the present invention also is not particularly limited.

<Process for Producing Amplification Products>

As described above, the process for producing amplification products of the present invention is a process for producing amplification products of two types of genes by the gene amplification method, wherein the two types of genes are the CYP2C9 gene and the VKORC1 gene, and the process includes the following step (I):

(I) amplifying the CYP2C9 gene and the VKORC1 gene simultaneously in the same reaction solution using a primer set for gene amplification according to the present invention, with nucleic acid contained in a sample being used as a template.

As described above, when an amplification reaction is carried out with a primer set of the present invention, the respective target regions of the CYP2C9 gene and the VKORC1 gene can be amplified simultaneously and specifically in the same reaction solution. As described above, the two target regions to be amplified according to the present invention are regions including sites to be detected where target polymorphisms are present in the CYP2C9 gene and the VKORC1 gene, respectively. The process for producing amplification products of the present invention is characterized by using a primer set of the present invention, and for example, the type of and conditions for the gene amplification method are not limited by any means.

The gene amplification method is not particularly limited as described above. Examples thereof include a polymerase chain reaction (PCR) method, a nucleic acid sequence based amplification (NASBA) method, a transcription-mediated amplification (TMA) method, and a strand displacement amplification (SDA) method, and the PCR method is preferable. The present invention is described below using the PCR method as an example but is not limited thereto.

The sample to which the present invention is to be applied is not particularly limited as long as it contains, for example, nucleic acid to serve as a template. However, it is preferable that the present invention be applied to, for example, a contaminated sample. Examples of the contaminated sample include whole blood, cells in the mouth (for example, oral mucosa), somatic cells of nails and hairs, germ cells, expectoration, amniotic fluid, paraffin-embedded tissue, urine, gastric juice (for example, gastric lavage fluid), and suspensions thereof. According to the process for producing amplification products using a primer set of the present invention, for example, even in the case of a sample (particularly, a biological sample such as whole blood or cells in the mouth) containing various contaminants, the process tends not to be affected thereby and allows the respective target regions in the two types of genes (the CYP2C9 gene and the VKORC1 gene) to be amplified specifically. Thus, according to the present invention, even a highly contaminated sample, which is difficult to use in conventional methods, can be used directly, for instance, without being pretreated, for example, without being purified. Therefore, it can be said also from the viewpoint of the pretreatment of the sample that amplification products can be prepared quicker as compared to conventional methods.

The ratio of the sample to be added to the reaction solution is not particularly limited. Specifically, when the sample is a biological sample (for example, a whole blood sample), the lower limit of the ratio thereof to be added to the reaction solution is, for example, preferably at least 0.01 vol %, more preferably at least 0.05 vol %, and further preferably at least 0.1 vol %. Furthermore, the upper limit of the ratio thereof to be added also is not particularly limited and is, for example, preferably 2 vol % or lower, more preferably 1 vol % or lower, and further preferably 0.5 vol % or lower.

When an optical detection to be described later is intended to be performed, particularly, when an optical detection is performed using a labeled probe, it is preferable that the ratio of a biological sample, such as a whole blood sample, to be added be set at, for example, 0.1 to 0.5 vol %. Generally, in the PCR reaction, a heat treatment is carried out to denature DNA (i.e. to dissociate it into a single-stranded DNA). This heat treatment may denature, for example, sugar or protein contained in the sample and thereby may generate, for example, an insoluble precipitate or turbidity. Therefore, when the presence or absence of an amplification product or the genotype (polymorphism) of a site to be detected is checked by an optical method, the generation of such a precipitate or turbidity may affect measurement accuracy. However, when the ratio of the whole blood sample to be added to the reaction solution is set in the range described above, for instance, the generation of, for example, a precipitate due to denaturation can be prevented sufficiently, although the mechanism thereof is unknown, and thereby the accuracy of measurement carried out by the optical method can be improved. Furthermore, since inhibition of PCR due to the contaminants contained in a whole blood sample also can be prevented sufficiently, the amplification efficiency can be improved further. Accordingly, when in addition to the use of a primer set of the present invention, the ratio of the sample such as a whole blood sample to be added is set in the aforementioned range, further the need to pretreat the sample can be omitted.

Furthermore, the ratio of the whole blood sample in the aforementioned reaction solution also can be indicated not in terms of the aforementioned volume ratio (for example, 0.1 to 0.5 vol %) but in a weight ratio of hemoglobin (hereinafter referred to as "Hb"). In this case, the ratio of the whole blood sample in the reaction solution is, for example, preferably in the range of 0.565 to 113 g/L, more preferably in the range of 2.825 to 56.5 g/L, and further preferably in the range of 5.65 to 28.25 g/L, in terms of the amount of Hb. The ratio of the whole blood sample to be added to the reaction solution may satisfy both the volume ratio and the Hb weight ratio or may satisfy one of them, for example.

The whole blood may be any one of, for example, hemolyzed whole blood, unhemolyzed whole blood, anticoagulated whole blood, and whole blood containing coagulated fractions.

In the present invention, the target nucleic acid contained in a sample is, for example, DNA. The aforementioned DNA may be DNA contained originally in the sample, such as a biological sample, or an amplification product DNA obtained through amplification by a gene amplification method. In the latter case, an example thereof is cDNA that is generated from RNA (for example, total RNA or mRNA) contained originally in the sample by a reverse transcription reaction (for instance, reverse transcription PCR (RT-PCR)).

In the process for producing amplification products of the present invention, it is preferable that albumin be added to the reaction solution before the start of a gene amplification reaction. Such addition of albumin further can reduce, for example, the generation of a precipitate or turbidity described above and also further can improve the amplification efficiency. Specifically, it is preferable that albumin be added before a step of synthesis (a step of amplification) of an extended strand by DNA polymerase or a step of dissociation into a single-stranded DNA.

The ratio of albumin to be added to the reaction solution is, for example, in the range of 0.01 to 2 wt %, preferably 0.1 to 1 wt %, and more preferably 0.2 to 0.8 wt %. The albumin is not particularly limited, and examples thereof include bovine serum albumin (BSA), human serum albumin, rat serum albumin, and horse serum albumin. Any one of them may be used or two or more of them may be used in combination.

Next, a process for producing amplification products of the present invention is described using an example in which, with respect to a whole blood sample including DNA to serve as target nucleic acid, respective amplification products of two types of genes, i.e. the CYP2C9 gene and the VKORC1 gene, are produced simultaneously in the same reaction solution by PCR. The present invention is characterized by using a primer set of the present invention and other configurations and conditions are not limited by any means.

First, a PCR reaction solution is prepared. The ratio of the primer sets of the present invention to be added is not particularly limited. However, F primers of the primer sets (1) and (2) each are added to be preferably 0.1 to 2 µmol/L, more preferably 0.25 to 1.5 µmol/L, and particularly preferably 0.5 to 1 µmol/L. Furthermore, R primers of the primer sets (1) and (2) each are added to be preferably 0.1 to 2 µmol/L, more preferably 0.25 to 1.5 µmol/L, and particularly preferably 0.5 to 1 µmol/L. The ratio (F:R, molar ratio) between the F primer and the R primer to be added to each primer set is not particularly limited. It is, for example, preferably 1:0.25 to 1:4 and more preferably 1:0.5 to 1:2.

The ratio of the whole blood sample in the reaction solution is not particularly limited but is preferably in the range described above. The whole blood sample may be added directly to the reaction solution or may be added to the reaction solution after being diluted with a solvent such as water or a buffer solution beforehand. When the whole blood sample is diluted beforehand, the dilution ratio is not particularly limited. It can be set so that, for example, the final ratio of the whole blood added to the reaction solution is in the aforementioned range, for example, 1:100 to 1:2000 and preferably 1:200 to 1:1000.

Other composition components in the reaction solution are not particularly limited and can be conventionally known components whose ratios also are not particularly limited. Examples of the composition components include DNA polymerase, nucleoside triphosphate, and a solvent. Furthermore, as described above, it is preferable that the reaction solution further contain albumin. In the reaction solution, the order of addition of the respective composition components is not limited by any means.

The DNA polymerase is not particularly limited and, for example, a conventionally known thermoduric bacteria-derived polymerase can be used. Specifically, for example, *Thermus aquaticus*-derived DNA polymerase (U.S. Pat. No. 4,889,818 and U.S. Pat. No. 5,079,352) (trade name: Taq polymerase), *Thermus thermophilus*-derived DNA polymerase (WO 91/09950) (rTth DNA polymerase), *Pyrococcus furiosus*-derived DNA polymerase (WO 92/9689) (Pfu DNA polymerase; manufactured by Stratagenes), and *Thermococcus litoralis*-derived DNA polymerase (EP-A 455 430) (Trademark: Vent; manufactured by New England Biolabs) are commercially available. Particularly, *Thermus aquaticus*-derived thermostable DNA polymerase is preferable.

The ratio of DNA polymerase to be added to the reaction solution is not particularly limited and is, for example, 1 to 100 U/mL, preferably 5 to 50 U/mL, and more preferably 20 to 30 U/mL. With respect to the unit of activity (U) of DNA polymerase, generally, 1 J denotes the activity that allows all 10 nmol of nucleotide to be taken into an acid-insoluble precipitate in 30 minutes at 74° C. in a reaction solution for activity measurement (25 mM TAPS buffer (pH 9.3, 25° C.), 50 mM KCl, 2 mM $MgCl_2$, 1 mM mercaptoethanol, 200 µM dATP, 200 µM dGTP, 200 µM dTTP, 100 µM "α-$^{32}$P" dCTP, and 0.25 mg/mL activated salmon sperm DNA), with an activated salmon sperm DNA being used as a template primer.

Generally, examples of the nucleoside triphosphate include dNTP (dATP, dGTP, dCTP, and dTTP). The ratio of dNTP to be added to the reaction solution is not particularly limited and is, for example, 0.01 to 1 mmol/L, preferably 0.05 to 0.5 mmol/L, and more preferably 0.1 to 0.3 mmol/L.

Examples of the aforementioned solvent include buffer solutions such as Tris-HCl, Tricine, MES, MOPS, HEPES, and CAPS. Commercially available PCR buffer solutions or buffer solutions of commercially available PCR kits can be used.

Furthermore, the PCR reaction solution further may contain glycerol, heparin, betaine, KCl, $MgCl_2$, $MgSO_4$, and glycerol. The ratios thereof to be added can be set in ranges in which the PCR reaction is not inhibited.

The total volume of the reaction solution is not particularly limited and can be determined suitably according to, for example, the equipment (thermal cycler) to be used. It is generally 1 to 500 µL and preferably 10 to 100 µL.

Subsequently, PCR is performed. The cycle conditions in PCR are not particularly limited, and, for example, (1) dissociation of whole blood-derived double-stranded DNA into a single-stranded DNA, (2) annealing of a primer, and (3) elongation of a primer (polymerase reaction) are as described below. Furthermore, the number of cycles also is not particularly limited but preferably is at least 30, with the following three steps (1) to (3) being considered as one cycle. The upper limit thereof, in total, is not particularly limited and is, for example, 100 cycles or less, preferably 70 cycles or less, and further preferably 50 cycles or less. The change in temperature in each step can be controlled automatically using, for example, a thermal cycler. In the case of using a primer set of the present invention, since they are excellent in amplification efficiency as described above, 50 cycles can be completed in approximately one hour (preferably within one hour) according to the present invention, while it takes approximately three hours to complete 50 cycles according to conventional methods.

TABLE 3

| | Temperature (° C.) and Time (sec) |
|---|---|
| (1) Dissociation of single-stranded DNA | For example, 90 to 99° C., 1 to 120 sec<br>Preferably, 92 to 95° C., 1 to 60 sec |
| (2) Annealing of primer | For example, 40 to 70° C., 1 to 300 sec<br>Preferably, 50 to 70° C., 5 to 60 sec |
| (3) Elongation reaction | For example, 50 to 80° C., 1 to 300 sec<br>Preferably, 50 to 75° C., 5 to 60 sec |

In the manner described above, amplification products of the respective target regions of the CYP2C9 gene and the VKORC1 gene can be produced simultaneously in the same reaction solution.

The process for producing amplification products of the present invention further may include a step of detecting amplification products obtained through the aforementioned amplification reaction. This makes it possible to detect the presence or absence of the amplification products or the genotypes in the respective target regions of the respective genes. The presence or absence of the amplification products can be checked by a conventionally known method. Specifically, it can be checked by, for example, further adding a probe (for instance, a fluorescently-labeled probe) capable of hybridizing to a site to be detected in the CYP2C9 gene or the VKORC1 gene to the reaction solution in step (I) described above, and further in step (II), measuring the fluorescence intensity of the fluorescent label in the probe with respect to the reaction solution. Furthermore, when the presence or absence of amplification products of both the CYP2C9 gene and the VKORC1 gene is to be checked, it can be checked by further adding respective probes for the respective genes, and in step (II), measuring the fluorescence intensities of the respective fluorescent labels in the respective probes with respect to the reaction solution. On the other hand, detection of polymorphisms in the CYP2C9 gene and the VKORC1 gene is described below as an embodiment of the present invention.

<Method of Analyzing CYP2C9 Genetic Polymorphism and VKORC1 Genetic Polymorphism>

The genetic polymorphism analysis method of the present invention is a method of analyzing the polymorphisms of sites to be detected in respective genes using the same reaction solution, with the genes being the CYP2C9 gene and the VKORC1 gene. The method is characterized by including the following steps (i) to (iv):

(i) simultaneously amplifying a region including a site to be detected in the CYP2C9 gene and a region including a site to be detected in the VKORC1 gene in the same reaction solution by a process for producing amplification products according to the present invention, (ii) preparing a reaction solution that contains the amplification product of the CYP2C9 gene and the amplification product of the VKORC1 gene obtained in step (i) as well as probes capable of hybridizing to the respective sites to be detected in the respective genes, (ii) measuring signal values that indicate melting states of the respective hybridization products between the respective amplification products and the respective probes while changing the temperature of the reaction solution, and (iv) determining polymorphisms of the respective sites to be detected from a change in the signal values accompanying a change in the temperature.

In this manner, when amplification products are produced using a primer set of the present invention, it is possible to amplify the regions including target sites of polymorphisms in the two types of genes, i.e. the CYP2C9 gene and the VKORC1 gene, as described above.

The probes to be used in step (ii) described above are not particularly limited. Examples thereof include a probe complementary to the sequence to be subjected to detection in the CYP2C9 gene (hereinafter also referred to as a "probe for the CYP2C9 gene") and a probe complementary to the sequence to be subjected to detection in the VKORC1 gene (hereinafter also referred to as a "probe for the VKORC1 gene"). Either one of the probes may be used, but it is preferable that both the probe for the CYP2C9 gene and the probe for the VKORC1 gene be used together because this allows the polymorphisms of the respective genes to be determined using the same reaction solution.

The probes for the respective CYP2C9 gene and VKORC1 gene are not particularly limited and can be determined according to a conventionally known method. For example, they may be designed as sequences to be subjected to detection containing sites to be detected of polymorphisms, based on the sequences of sense strands or the sequences of antisense strands of the respective genes. Furthermore, the base located at the site to be detected of a polymorphism can be determined suitably according to the type of each polymorphism.

In other words, in the case of the CYP2C9 gene, since the polymorphisms of A (CYP2C9*1) and C (CYP2C9*3) at base 521 in SEQ ID NO: 1 have been known, examples of the probe include a probe complementary to either a sequence to be subjected to detection including A at base 521 or a sequence to be subjected to detection including C at base 521 (a probe for detecting a sense strand), and a probe complementary to a sequence of an antisense strand thereof (a probe for detecting an antisense strand). Moreover, since the polymorphisms of T (CYP2C9*1) and C (CYP2C9*4) at base 522 in SEQ ID NO: 1 have been known, examples of the probe include a probe complementary to either a sequence to be subjected to detection including T at base 522 or a sequence to be subjected to detection including C at base 522 (a probe for detecting a sense strand), and a probe complementary to a sequence of an antisense strand thereof (a probe for detecting an antisense strand).

Furthermore, in the case of the VKORC1 gene, since the polymorphisms of "C" and "T" at base 484 in SEQ ID NO: 2 have been known, examples of the probe include a probe complementary to either a sequence to be subjected to detection including C at base 484 or a sequence to be subjected to detection including T at base 484 (a probe for detecting a sense strand), and a probe complementary to a sequence of an antisense strand thereof (a probe for detecting an antisense strand). As described above, even when a probe is designed, with the base located at the site to be detected where a polymorphism is generated being set to be any one of the bases as described above, it is possible to judge what type of polymorphism is expressed at each site to be detected in the respective genes by the method described later. Preferably, the probes are designed with consideration given to the tendencies of polymorphisms that are different between races. It also is possible to employ a method in which, for example, in the case of Japanese, a polymorphism of C is scarcely present at base 484 in SEQ ID NO: 2 and therefore the probe is designed, for example, to be perfectly matched with C at base 484, while in the case of Westerners, a polymorphism of C is often present at base 484 and therefore the probe is designed, for example, to be perfectly matched with T at base 484.

The respective probes can be added to a reaction solution after amplification reaction of the target regions of the respective genes. However, it is preferable that the probes be added to a reaction solution beforehand, for example, prior to the amplification reaction in step (i) described above, since this allows analysis to be performed easily and quickly.

In step (i), the ratio of the probes to be added to the reaction solution is not particularly limited. For example, each probe is added to be preferably in the range of 10 to 400 nmol and more preferably in the range of 20 to 200 nmol. When a fluorescent dye is used as the label for a probe, an unlabeled probe with a sequence identical to that of the labeled probe may be used in combination with the labeled probe, for example, in order to adjust the fluorescence intensity to be detected, and the unlabeled probe may include phosphoric acid added to the 3' end thereof. In this case, the molar ratio between the labeled probe and the unlabeled probe is preferably, for example, 1:10 to 10:1. The length of the probe is not particularly limited and is, for example, 5- to 50-mers and preferably 10- to 30-mers.

The Tm value is described. When a solution containing double-stranded DNA is heated, the absorbance at 260 nm increases. This is because heating releases the hydrogen bonds between both strands in the double-stranded DNA to dissociate it into single-stranded DNA (i.e. to melt DNA). When all double-stranded DNAs are dissociated into single-stranded DNAs, the absorbance indicated thereby is approximately 1.5 times that obtained at the start of heating (i.e. absorbance of only double-stranded DNAs), which makes it possible to judge that melting is completed thereby. Based on this phenomenon, the melting temperature Tm generally is defined as a temperature at which the absorbance has reached 50% of the total increase in absorbance.

In step (iii) described above, the measurement of the signals that indicate the melting states of the hybridization products between the amplification products and the probes may be a measurement of absorbance at 260 nm as described above, but may be a measurement of the signal of a labeling substance. Specifically, it is preferable that a labeled probe that has been labeled with a labeling substance be used as the aforementioned probe to perform the measurement of the signal of the labeling substance. The labeled probe can be, for example, a labeled probe that exhibits a signal independently and does not exhibit a signal after hybridization, or a labeled probe that does not exhibit a signal independently and exhibits a signal after hybridization. The former probe does not exhibit a signal after forming a hybrid (double-stranded DNA) with a sequence to be subjected to detection but exhibits a signal when the probe is released by heating. On the other hand, the latter probe exhibits a signal after forming a hybrid (double-stranded DNA) with a sequence to be subjected to detection but the signal is reduced (quenched) when the probe is released by heating. Accordingly, when the signal exhibited by this label is detected under a condition (for example, absorption wavelength) specific to the signal, the progress of melting of the hybridization product and the Tm value can be determined as in the case of the measurement of absorbance at 260 nm.

In the present invention, in order to check the respective polymorphisms with respect to two genes, it is preferable that two types of probes be labeled with different labels (for example, fluorescent labels) that are detected under different conditions, respectively. The use of different labels in this manner makes it possible to analyze the respective amplification products separately by changing the detection conditions even in the same reaction solution.

Specific examples of labeling substances in the labeled probes include a fluorescent dye (fluorophore). A specific example of the labeled probes is preferably a probe that, for example, has been labeled with a fluorescent dye, exhibits fluorescence independently, and allows fluorescence to be reduced (for example, quenched) after hybridization. Generally, a probe that utilizes such a fluorescence quenching phenomenon is referred to as a fluorescence quenching probe. Particularly, with respect to the aforementioned probe, it is preferable that the 3' end or 5' end of oligonucleotide be labeled with a fluorescent dye and the base located at the end to be labeled be C. In this case, it is preferable that the base sequence of the labeled probe be designed so that in the sequence to be subjected to detection, to which the labeled probe hybridizes, the base to be paired with the end base C of the labeled probe or the base located one to three bases apart from the base to be paired is G. Generally, such a probe is referred to as a guanine quenching probe and is known as so-called QProbe (registered trademark). When such a guanine quenching probe hybridizes to a sequence to be subjected to detection, C located at the end, which has been labeled with a fluorescent dye, approaches G in the DNA to be subjected to detection, and thereby a phenomenon occurs in which the emission of the fluorescent dye is reduced (the fluorescence intensity decreases). The use of such a probe makes it possible to verify hybridization and dissociation easily according to a change in the signal.

The fluorescent dye is not particularly limited. Examples thereof include fluorescein, phosphor, rhodamine, and polymethine dye derivative. Examples of commercially available fluorescent dye include BODIPY FL (brand name, manufactured by Molecular Probe Inc.), FluorePrime (trade name, manufactured by Amersham Pharmacia), Fluoredite (trade name, manufactured by Millipore Corporation), FAM (manufactured by ABI), Cy3 and Cy5 (manufactured by Amersham Pharmacia), and TAMRA (manufactured by Molecular Probe Inc.). The detection conditions are not particularly limited and can be determined suitably according to fluorescent dyes to be used. For example, PACIFIC BLUE can be detected with a detection wavelength of 450 to 480 nm, TAMRA can be detected with a detection wavelength of 585 to 700 nm and BODIPY FL can be detected with a detection wavelength of 515 to 555 nm.

Specific examples of the sequences of probes for analyzing (detecting) the respective polymorphisms of the aforementioned CYP2C9 gene and VKORC1 gene are indicated below, but the present invention is not limited thereto.

The following probe (1) is an example of a probe for the CYP2C9 gene. It is a probe for detecting a sense strand and consists of a sequence complementary to that of a region including C at base 521 in SEQ ID NO: 1. Furthermore, specific examples of the probes according to the present invention may be complementary strands of the oligonucleotides indicated below, as described above.

Probe (1)

At least one oligonucleotide having a sequence complementary to that of a region extending from guanine (G) at base 516 to be considered as the first base to any one of the $17^{th}$ to $22^{nd}$ bases in the direction toward the 3' end in SEQ ID NO: 1, with cytosine complementary to the guanine being the 3' end.

Specific examples of Probe (1) are indicated in the following table.

TABLE 4

| Primer | Sequence | Tm (° C.) | SEQ ID NO. |
|---|---|---|---|
| Probe (P1) | 5'-gtggggagaaggtcaAGgtatc-3' | 55.7 | 41 |
| | 5'-tggggagaaggtcaAGgtatc-3' | 54.4 | 42 |
| | 5'-ggggagaaggtcaAGgtatc-3' | 52.8 | 43 |

TABLE 4-continued

| Primer | Sequence | Tm (° C.) | SEQ ID NO. |
|---|---|---|---|
| | 5'-gggagaaggtcaAGgtatc-3' | 50.2 | 44 |
| | 5'-ggagaaggtcaAGgtatc-3' | 47.3 | 45 |
| | 5'-gagaaggtcaAGgtatc-3' | 44.1 | 46 |

It also is possible to detect the polymorphism (CYP2C9*4) at base 522 in SEQ ID NO: 1 using the aforementioned probe for the CYP2C9 gene. For example, the probe for the CYP2C9 gene has a sequence complementary to that of a region having C at base 521 and T at base 522 in SEQ ID NO: 1. That is, it is judged that the polymorphism is CYP2C9*3 (A521C) in the case of perfectly matching with this probe, it is CYP2C9*1 (wildtype) in the case of mismatching by one base, and it is CYP2C9*4 (T522C) in the case of mismatching by two bases.

The capitalized base G in each probe indicated in the above table can be replaced by "k", and the "k" can be either G or T. Furthermore, the capitalized A can be replaced by "r", and the "r" can be either A or G.

Examples of the probe for the VKORC1 gene include the probes (2-1) and (2-2) indicated below. The probe (2-1) indicated below is a probe for detecting an antisense strand and consists of a sequence identical to that of a region having C at base 484 in SEQ ID NO: 2. On the other hand, the probe (2-2) indicated below is a probe for detecting a sense strand and consists of a sequence complementary to that of a region having C at base 484 in SEQ ID NO: 2. Specific examples of the probes according to the present invention may be complementary strands of the oligonucleotides indicated below, as described above.

Probe (2-1)

At least one oligonucleotide having a sequence identical to that of a region extending from cytosine (C) at base 477 to be considered as the first base to any one of the $18^{th}$ to $24^{th}$ bases in the direction toward the 3' end in SEQ ID NO: 2, with the cytosine being the 5' end.

Probe (2-2)

At least one oligonucleotide having a sequence complementary to that of a region extending from guanine (G) at base 472 to be considered as the first base to any one of the $15^{th}$ to $24^{th}$ bases in the direction toward the 3' end in SEQ ID NO: 2, with cytosine complementary to the guanine being the 3' end.

In the following table, SEQ ID NOs: 47 to 53 and SEQ ID NOs: 54 to 63 are indicated as specific examples of Probe (2-1) and Probe (2-2), respectively.

TABLE 5

| Primer | Sequence | Tm (° C.) | SEQ ID NO. |
|---|---|---|---|
| Probe (P2) | 5'-catcgacCcttggactaggatggg-P-3' | 59.7 | 47 |
| | 5'-catcgacCcttggactaggatgg-P-3' | 57.9 | 48 |
| | 5'-catcgacCcttggactaggatg-P-3' | 55.8 | 49 |
| | 5'-catcgacCcttggactaggat-P-3' | 54.6 | 50 |
| | 5'-catcgacCcttggactagga-P-3' | 54.3 | 51 |
| | 5'-catcgacCcttggactagg-P-3' | 52.9 | 52 |
| | 5'-catcgacCcttggactag-P-3' | 50.2 | 53 |
| | 5'-cctagtccaagGgtcgatgatctc-3' | 57.5 | 54 |
| | 5'-ctagtccaagGgtcgatgatctc-3' | 55.5 | 55 |
| | 5'-tagtccaagGgtcgatgatctc-3' | 54.6 | 56 |
| | 5'-agtccaagGgtcgatgatctc-3' | 54.9 | 57 |
| | 5'-gtccaagGgtcgatgatctc-3' | 53.6 | 58 |
| | 5'-tccaagGgtcgatgatctc-3' | 52.1 | 59 |
| | 5'-ccaagGgtcgatgatctc-3' | 50.6 | 60 |
| | 5'-caagGgtcgatgatctc-3' | 47.6 | 61 |
| | 5'-aagGgtcgatgatctc-3' | 45.4 | 62 |
| | 5'-agGgtcgatgatctc-3' | 44.0 | 63 |

In the respective probes of SEQ ID NOs: 47 to 53 indicated in the above table, the capitalized base C can be replaced by "y" and the "y" can be either C or T. On the other hand, in the respective probes of SEQ ID NOs: 54 to 63 indicated in the above table, the capitalized base G can be replaced by "r" and the "r" can be either G or A.

As described above, it is preferable that these probes be labeled with different fluorescent dyes (fluorescent dyes that are detected at different wavelengths), respectively. For example, when the probes indicated in the above table are quenching probes, it is preferable that in the probe (1) for the CYP2C9 gene, cytosine at the 3' end thereof be labeled with a fluorescent dye described above (for example, BODIPY FL), and in the probes (2-1) and (2-2) for the VKORC1 gene, cytosine at the 5' end and cytosine at the 3' end be labeled with fluorescent dyes described above (for example, PACIFIC BLUE), respectively. Furthermore, in the case of a probe with the 5' end labeled with a fluorescent dye, a phosphoric acid group further may be added to the 3' end thereof, for example, in order to prevent the probe itself from elongating.

The aforementioned probes are merely examples and the present invention is not limited by these at all. However, the probe for the CYP2C9 gene is preferably a probe consisting of a base sequence of SEQ ID NO: 44 or a probe consisting of a base sequence of SEQ ID NO: 45 described above, while the probe for the VKORC1 gene is preferably a probe consisting of a base sequence of SEQ ID NO: 51 or a probe consisting of a base sequence of SEQ ID NO: 62 described above.

Next, with respect to an analysis method of the present invention, a method of detecting a polymorphism of the CYP2C9 gene (CYP2C9*3, a polymorphism of base 521 in SEQ ID NO: 1) and a polymorphism of the VKORC1 gene (C6484T, a polymorphism of base 484 in SEQ ID NO: 2) using the following probes is described as examples. However, the present invention is not limited thereby.

(P1) oligonucleotide consisting of the base sequence of SEQ ID NO: 44 or oligonucleotide consisting of the base sequence of SEQ ID NO: 45

```
5'-gggagaaggtcaaGgtatc-(BODIPY FL)-3'
5'-ggagaaggtcaaGgtatc-(BODIPY FL)-3'
```

(P2) oligonucleotide consisting of the base sequence of SEQ ID NO: 51 or oligonucleotide consisting of the base sequence of SEQ ID NO: 62

```
5'-(PACIFIC BLUE)-catcgacCcttggactagga-P-3'
5'-aagGgtcgatgatctc-(PACIFIC BLUE)-3'
```

First, using a reaction solution containing the aforementioned two types of labeled probes added thereto, PCR was performed as described above, and thereby the respective target regions of the CYP2C9 gene and the VKORC1 gene are amplified simultaneously in the same reaction solution. The reaction solution contains, for example, a primer set of the present invention, DNA polymerase, dNTP, a sample containing nucleic acid to serve as a template, and the aforementioned probes. In addition to these, various additives that can be used for amplifying nucleic acid may be contained.

Next, the amplification products thus obtained are dissociated and then single-stranded DNAs obtained through dissociation are hybridized with the labeled probes. This can be carried out through, for example, a change in the temperature of the reaction solution.

The heating temperature employed in the dissociation step is not particularly limited as long as it allows the amplification products to be dissociated. It is, for example, 85 to 95° C. The heating time also is not particularly limited and generally is 1 second to 10 minutes and preferably 1 second to 5 minutes.

The dissociated single-stranded DNAs can be hybridized with the labeled probes by, for example, decreasing the heating temperature employed in the dissociation step after the dissociation step. The temperature condition is, for example, 40 to 50° C.

Thereafter, while the temperature of the reaction solution is changed, signal values that indicate the melting states of hybridization products between the amplification products and the labeled probes are measured. Specifically, for example, while the reaction solution (the hybridization products between the single-stranded DNAs and the labeled probes) is heated, the change in the signal accompanying the temperature rise is measured. As described above, when, for example, a probe (guanine quenching probe) in which the base C at the end has been labeled is used, fluorescence decreases (or quenches) in the state where the probe has been hybridized with the single-stranded DNA, while fluorescence is emitted in the state where the probe has been dissociated. Accordingly, for example, while the hybridization product in which the fluorescence has decreased (or quenched) is heated gradually, the increase in fluorescence intensity accompanying the temperature rise may be measured.

The temperature range over which the change in fluorescence intensity is measured is not particularly limited. For example, the start temperature is room temperature to 85° C. and preferably 25 to 70° C., while the end temperature is, for example, 40 to 105° C. Furthermore, the rate of temperature rise is not particularly limited and is, for example, 0.1 to 20° C./sec and preferably 0.3 to 5° C./sec.

Next, the Tm value is determined by analyzing a change in the signal. Specifically, the amount of change in the fluorescence intensity per unit time at each temperature (–d fluorescence intensity increase/dt) is calculated from the resultant fluorescence intensity and the temperature at which the lowest value is obtained can be determined as the Tm value. The point at which the amount of increase in the fluorescence intensity per unit time (fluorescence intensity increase/t) is the highest also can be determined as the Tm value. On the contrary, the amount of decrease in the fluorescence intensity can be measured when the labeled probe used is not a quenching probe but a probe that does not exhibit a signal independently and exhibits a signal after hybridization.

In the present invention, in order to detect the respective polymorphisms of the two genes, the respective Tm values are determined under conditions suitable for the respective labels of the two types of probes. BODIPY FL of a probe for the CYP2C9 gene can be detected with, for example, a detection wavelength of 515 to 555 nm, and PACIFIC BLUE of a probe for the VKORC1 gene can be detected with, for example, a detection wavelength of 450 to 480 nm.

From these Tm values, the genotypes at the sites to be detected in the respective genes are determined. In the Tm analysis, a perfectly complementary hybrid (match) results in a higher Tm value indicating dissociation than that obtained in the case of a hybrid including a different single base (mismatch). Accordingly, when with respect to the aforementioned probes, the Tm value of a perfectly complementary hybrid and the Tm value of a hybrid including a different single base are determined beforehand, the genotype at each site to be detected can be determined. For example, in the case where the base located at the target site in a sequence to be subjected to detection is assumed to be of a mutation type (with, for instance, C at base 521 in SEQ ID NO: 1), when using a probe complementary to the sequence to be subjected to detection containing the base, the polymorphism of the amplification product can be judged to be a mutation type if the Tm value of the resultant hybrid is equal to the Tm value of a perfectly complementary hybrid. Furthermore, the polymorphism of the amplification product can be judged to be a wildtype (with, for example, A at base 521 in SEQ ID NO: 1) if the Tm value of the resultant hybrid is equal to the Tm value of the hybrid including a different single base i.e. a lower Tm value than that of the perfectly complementary hybrid). Moreover, when both the Tm values are detected, it can be judged to be a heterozygote. Thus, the respective polymorphisms of the CYP2C9 gene and the VKORC1 gene can be judged from the two Tm values obtained with respect to the respective labeled probes.

Specifically, when using the aforementioned probes (P1 and P2), the following judgment can be made. In the aforementioned probe P1 described as an example of a probe for detecting the CYP2C9 gene, the base corresponding to base 521 in SEQ ID NO: 1 is set to be G. Accordingly, when the Tm value of the resultant hybrid is equal to that of a perfectly complementary hybrid, the polymorphism of the amplification product can be judged to be a mutation type (CYP2C9*3). On the other hand, when the Tm value of the resultant hybrid is equal to that of a hybrid including a different single base (i.e. a lower Tm value than that of the perfectly complementary hybrid), the polymorphism of the amplification product can be judged to be a wildtype (CYP2C9*1). Furthermore, when both the Tm values are detected, it can be concluded to be a heterozygote. On the other hand, in the aforementioned probe P2 described as an example of a probe for detecting the VKORC1 gene, base 6484 of the full-length sequence of the VKORC1 (base 484 in SEQ ID NO: 2) is set to be C. Accordingly, when the Tm value of the resultant hybrid is equal to that of a perfectly complementary hybrid, the polymorphism of the amplification product can be judged to be a wildtype (C6484C). On the other hand, when the Tm value of the resultant hybrid is equal to that of a hybrid including a different single base (i.e. a lower Tm value than that of the perfectly complementary hybrid), the polymorphism of the amplification product can be judged to be a mutation type (C6484T). Furthermore, when both the Tm values are detected, it can be concluded to be a heterozygote.

In the present invention, for example, a change in the signal during hybridization may be measured instead of the method in which, while the hybridization product is heated, a change in the signal accompanying the temperature rise is measured as described above. In other words, when the temperature of the reaction solution containing the aforementioned probes is decreased to form hybridization products, the change in the signal accompanying the temperature decrease may be measured.

Specifically, when using a labeled probe that exhibits a signal independently and does not exhibit a signal after hybridization (for example, a guanine quenching probe), the labeled probe emits fluorescence in the state where single-stranded DNA and the probe are dissociated, but the fluorescence decreases (or quenches) when a hybrid is formed through temperature decrease. Accordingly, for example, the temperature of the reaction solution is decreased gradually and the decrease in fluorescence intensity accompanying the temperature decrease may be measured. On the other hand, when using a labeled probe that does not exhibit a signal independently and exhibits a signal after hybridization, the labeled probe does not emit fluorescence in the state where single-stranded DNA and the probe are dissociated, but the fluorescence is emitted when a hybrid is formed through temperature decrease. Accordingly, for example, while the temperature of the reaction solution is decreased gradually, the increase in fluorescence intensity accompanying the temperature decrease may be measured.

Next, examples of the present invention are described. However, the present invention is not limited by the following examples.

Example 1

Blood was collected from two subjects using heparin lithium blood collection tubes (Samples 1 and 2). Subsequently, 0.1 µL of blood thus obtained was added to 50 µL of PCR reaction solution having the composition described below, and then PCR was performed using a thermal cycler. Conditions for PCR were as follows. That is, after it was treated at 95° C. for 60 seconds, one cycle of treatment at 95° C. for 1 second and at 58° C. for 15 seconds was repeated for 50 cycles, and further it was treated at 95° C. for 1 second and at 40° C. for 60 seconds. Subsequently, the PCR reaction solution was heated from 40° C. to 95° C. at a rate of temperature climb of 1° C./3 seconds, and the change in fluorescence intensity over time was measured. The measurement wavelengths were 450 to 480 nm (for detection of the fluorescent dye, PACIFIC BLUE) and 515 to 555 nm (for detection of the fluorescent dye, BODIPY FL). The time required for 50 cycles of PCR was approximately one hour.

TABLE 6

<PCR reaction solution>

| | |
|---|---|
| Distilled water | 23.25 |
| 5% NaN$_3$ | 0.5 |
| 20% BSA | 1 |
| 40% Glycerol | 12.5 |
| 10 × Gene Taq buffer * | 5 |
| 2.5 mM dNTPs | 4 |
| 5 µM probe for CYP2C9 | 1 |
| 100 µM CYP2C9 F1 primer | 0.5 |
| 100 µM CYP2C9 R1 primer | 0.25 |
| 5 µM probe for VKORC1 | 1 |
| 100 µM VKORC1 F2 primer | 0.25 |
| 100 µM VKORC1 R2 primer | 0.5 |
| 5 U/µl Gene Taq FP * | 0.25 |
| Total | 50 µL |

* Trade name, Gene Taq Fp: manufactured by Nippon Gene Co., Ltd. (the same applies below)

<Probes>

```
Probe for CYP2C9
                                      (SEQ ID No: 44)
5'-gggagaaggtcaaGgtatc-(BODIPY FL)-3'

Probe for VKORC1 gene
                                      (SEQ ID NO: 51)
5'-(PACIFIC BLUE)-catcgacCcttggactagga-P-3'
```

<Primer Set>

```
         CYP2C9 F1 primer
                                       (SEQ ID NO: 5)
         5'-gagccctgcatgcaa-3'

CYP2C9 R1 primer
                                       (SEQ ID NO: 18)
         5'-gatactatgaatttggggacttcgaa-3'

VKORC1 gene F2 primer
```

```
                                       (SEQ ID NO: 29)
5'-gaggatagggtcagtgacatggaa-3'

VKORC1 gene R2 primer
                                       (SEQ ID NO: 38)
5'-ccctgcccgagaaaggtgat-3'
```

The Tm value of a hybrid that matches with the probe for the CYP2C9 is 59° C. (*3 in the following respective drawings) and that of a hybrid that mismatches therewith is 54° C. (*1 in the following respective drawings). The Tm value of a hybrid that matches with the probe for the VKORC1 gene is 61.0° C. (C in the following respective drawings) and that of a hybrid that mismatches therewith is 53.0° C. (T in the following respective drawings).

The respective results of Samples 1 and 2 are indicated in FIG. 1. These drawings show graphs of Tm analysis that indicate the changes in fluorescence intensity accompanying temperature rise. The differential value of the vertical axis indicates "–d fluorescence intensity increase/dt", while the horizontal axis indicates temperature (the same applies below). As shown in FIG. 1, the respective polymorphisms of the CYP2C9 gene and the VKORC1 gene in the respective samples were determined from the peaks of the signals. In order to support these results obtained from this example, with respect to the two subjects, the respective polymorphisms of the CYP2C9 and the VKORC1 genes were confirmed by the RFLP method. As a result, the same results as those obtained in this example were obtained. Accordingly, the use of a primer set of the present invention made it possible to amplify the CYP2C9 gene and the VKORC1 gene simultaneously in the same reaction solution using a whole blood sample that had not been pretreated and to analyze the respective polymorphisms of the genes using the same reaction solution.

Example 2

Buccal cells were collected with swabs from two subjects and each were then suspended in 500 µL of sterile distilled water (Samples 3 and 4). Thereafter 2.5 µL of each suspension was added to 47.5 µL of PCR reaction solution having the composition described below, and then PCR was performed and the change in fluorescence intensity over time was measured in the same manner as in Example 1. The measurement wavelengths were 450 to 480 nm (for detection of the fluorescent dye, PACIFIC BLUE) and 515 to 555 nm (for detection of the fluorescent dye, BODIPY FL). The time required for 50 cycles of PCR was approximately one hour.

TABLE 7

<PCR reaction solution>

| | |
|---|---|
| Distilled water | 20.75 |
| 5% NaN$_3$ | 0.5 |
| 20% BSA | 1 |
| 40% Glycerol | 12.5 |
| 10 × Gene Taq buffer * | 5 |
| 2.5 mM dNTPs | 4 |
| 5 µM probe for CYP2C9 | 1 |
| 100 µM CYP2C9 F1 primer | 0.5 |
| 100 µM CYP2C9 R1 primer | 0.25 |
| 5 µM probe for VKORC1 | 1 |
| 100 µM VKORC1 F2 primer | 0.25 |
| 100 µM VKORC1 R2 primer | 0.5 |
| 5 U/µl Gene Taq FP * | 0.25 |
| Total | 47.5 µL |

Figure 2:
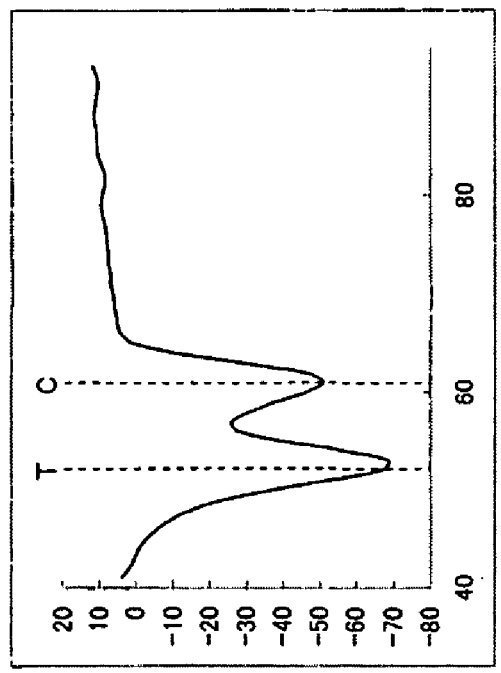
FIG. 2 shows graphs indicating the results of Tm analysis in another example of the present invention.
Figure 2:
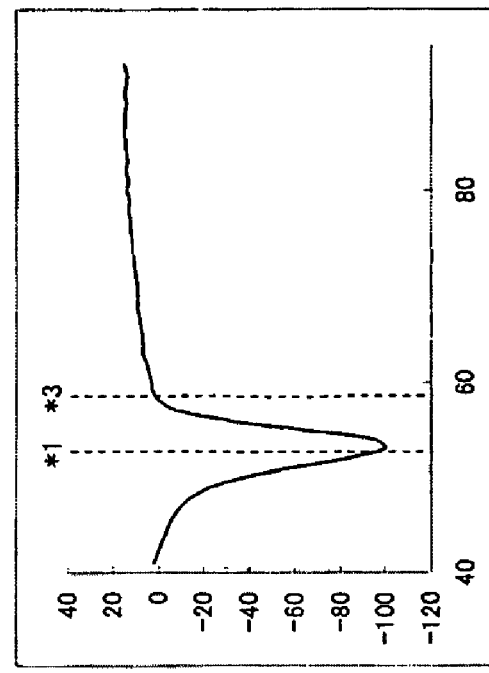
Figure 2:
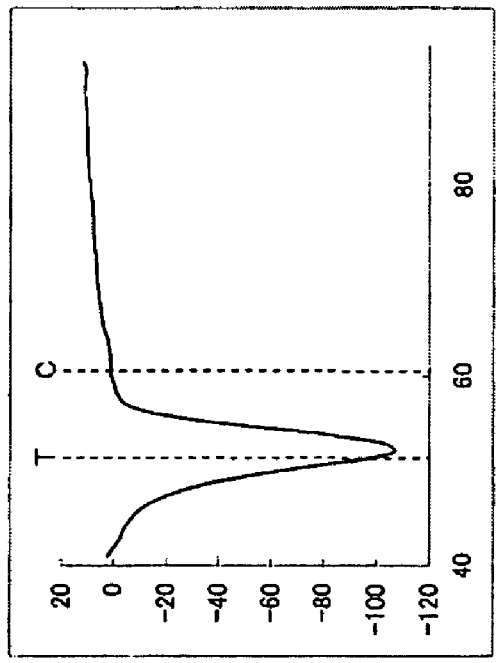
Figure 2:
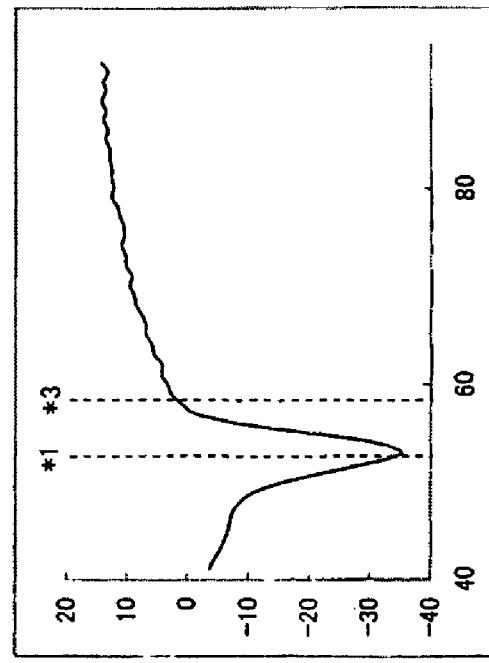

The respective results of Samples 3 and 4 are shown in FIG. 2. As shown in FIG. 2, the respective polymorphisms of the CYP2C9 gene and the VKORC1 gene in the respective samples were determined from the peaks of the signals. In order to support these results obtained from this example, with respect to the two subjects, the respective polymorphisms of the CYP2C9 and the VKORC1 genes were confirmed by the RFLP method. As a result, the same results as those obtained in this example were obtained. Accordingly, the use of a primer set of the present invention made it possible to amplify the CYP2C9 gene and the VKORC1 gene simultaneously in the same reaction solution using a buccal cell sample that had not been pretreated and to analyze the respective polymorphisms of the genes using the same reaction solution.

Example 3

Purified human genome was prepared in which base 521 in SEQ ID NO: 1 exhibited a heterozygote of CYP2C9*1/*3 (521A/521C) and base 6484 of the VKORC1 gene (base 484 in SEQ ID NO: 2) exhibited a homozygote of 6484T/T. Thereafter, 1 μL of this purified genome was mixed with 49 μL of PCR reaction solution having the composition described below, and then PCR was performed and the change in fluorescence intensity over time was measured in the same manner as in Example 1. The measurement wavelengths were 450 to 480 nm (for detection of the fluorescent dye, PACIFIC BLUE) and 515 to 555 nm (for detection of the fluorescent dye, BODIPY FL). The time required for 50 cycles of PCR was approximately one hour.

TABLE 8

| <PCR reaction solution> | |
| --- | --- |
| Distilled water | 22.25 |
| 5% NaN$_3$ | 0.5 |
| 20% BSA | 1 |
| 40% Glycerol | 12.5 |
| 10 × Gene Taq buffer * | 5 |
| 2.5 mM dNTPs | 4 |
| 5 μM probe for CYP2C9 | 1 |
| 100 μM CYP2C9 F1 primer | 0.5 |
| 100 μM CYP2C9 R1 primer | 0.25 |
| 5 μM probe for VKORC1 | 1 |
| 100 μM VKORC1 F2 primer | 0.25 |
| 100 μM VKORC1 R2 primer | 0.5 |
| 5 U/μl Gene Taq FP * | 0.25 |
| Total | 49 μL |

Figure 3:
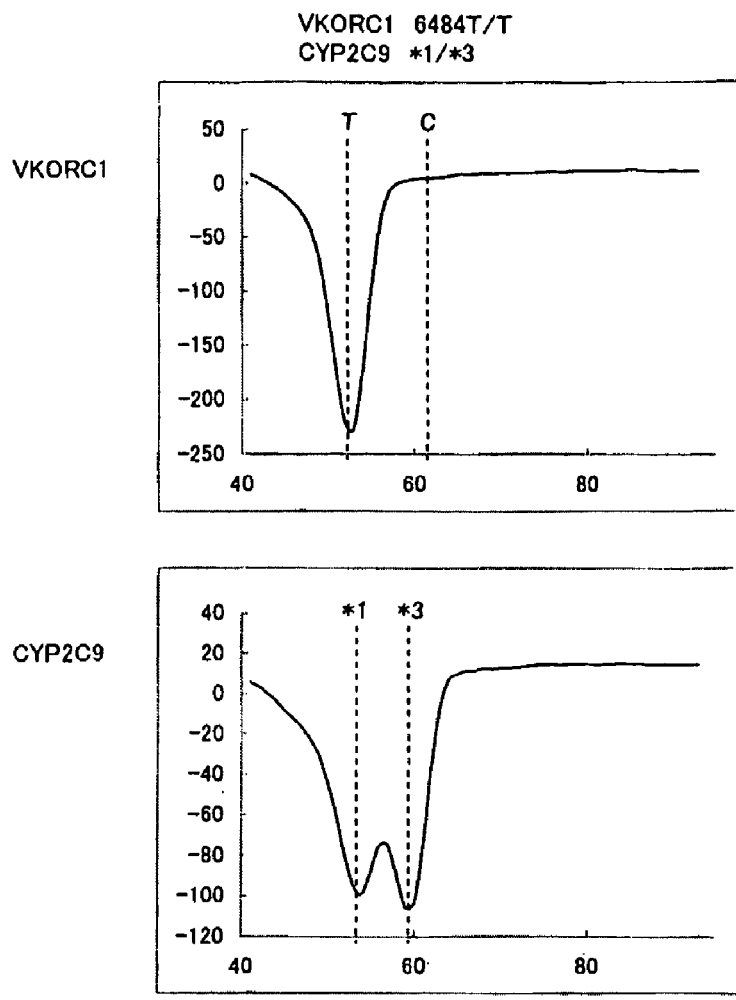
FIG. 3 shows graphs indicating the results of Tm analysis in still another example of the present invention.

The results are shown in FIG. 3. As shown in FIG. 3, two peaks were obtained with respect to the CYP2C9. Accordingly, it was proved that base 521 of SEQ ID NO: 1 was able to be differentiated to be detected. As shown in FIG. 3, the respective polymorphisms of the CYP2C9 gene and the VKORC1 gene in the respective samples were determined from the peaks of the signals. These results obtained from this example agreed with genomic information. Accordingly, the use of a primer set of the present invention made it possible to amplify the CYP2C9 gene and the VKORC1 gene simultaneously in the same reaction solution and to analyze the respective polymorphisms of the genes using the same reaction solution.

Example 4

Plasmid with the VKORC gene (CYP2C9*4) inserted thereinto was prepared, with the VKORC1 gene having C mutated from T at base 522 in SEQ ID NO: 1. Thereafter, 1 μL of this plasmid was mixed with 49 μL of PCR reaction solution that was identical to that used in Example 3, and then PCR was performed and the change in fluorescence intensity over time was measured in the same manner as in Example 1. The measurement wavelengths were 450 to 480 nm (for detection of the fluorescent dye, PACIFIC BLUE) and 515 to 555 nm (for detection of the fluorescent dye, BODIPY FL). The time required for 50 cycles of PCR was approximately one hour.

The Tm value of a hybrid that matches with the probe for the CYP2C9 is 60.0° C. (*3 in the following respective drawings), that of a hybrid that mismatches therewith by one base is 54° C. (*1 in the following respective drawings), and that of a hybrid that mismatches therewith by two bases is 49.0° C. (*4 in the following respective drawings).

Figure 4:
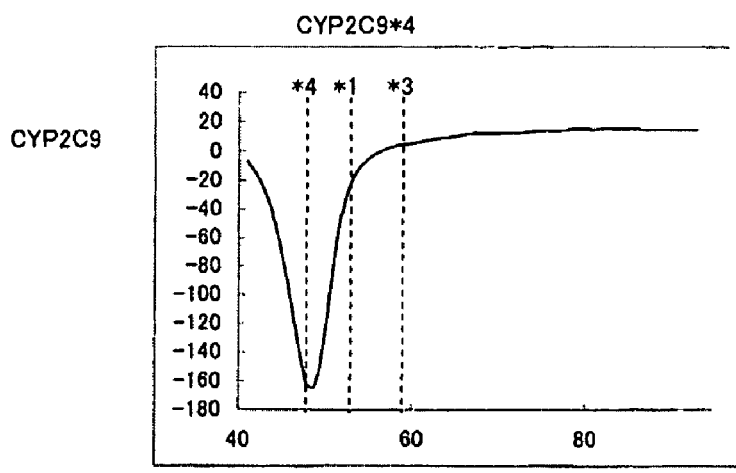
FIG. 4 shows a graph indicating the result of Tm analysis in yet another example of the present invention.

This result is shown in FIG. 4. As shown in FIG. 4, the peak was obtained at 49.0° C. Accordingly, it is proved that the PCR amplification product mismatched with the probe for the CYP2C9 gene by base 521 (i.e. base 521 is A) and base 522 (i.e. base 522 is C) in SEQ ID NO: 1. Therefore the polymorphism of the sample used for PCR was CYP2C9*4 and agreed with plasmid information.

Example 5

Purified human genome was prepared in which base 521 in SEQ ID NO: 1 exhibited a homozygote of CYP2C9*1/*1 (521A/521A) and base 6484 of the VKORC1 gene (base 484 in SEQ ID NO: 2) exhibited a homozygote of 6484T/T or 6484C/C or a heterozygote of 6484T/C. Thereafter, 1 μL of this purified genome was mixed with 46 μL of PCR reaction solution having the composition described below, and then PCR were performed and the change in fluorescence intensity over time were measured in the same manner as in Example 1. The measurement wavelengths were 450 to 480 nm (for detection of the fluorescent dye, PACIFIC BLUE) and 515 to 555 nm (for detection of the fluorescent dye, BODIPY FL). The time required for 50 cycles of PCR was approximately one hour.

Blood was collected from a patient in which base 521 in SEQ ID NO: 1 exhibited a homozygote of CYP2C9*1/*1 (521A/521A) and base 6484 of the VKORC1 gene (i.e. base 484 in SEQ ID NO: 2) exhibited a heterozygote of 6484T/C, using an EDTA blood collection tube. Thereafter 10 μL of blood and 70 μL of the following sample diluent 1 were mixed together and further 10 μL of the mixture and 70 μL of the following sample diluent 2 were mixed together. After 17 μL of this mixture was heat-treated at 95° C. for ten minutes, it was mixed with 46 μL of the following PCR reaction solution. PCR reaction and the change in fluorescence intensity over time were then measured in the same manner as in Example 1.
<Sample Diluent 1>
  10 mM Tris-HCl (pH 8), 0.1 mM EDTA, 0.3% SDS, 0.5% sodium azide
<Sample Diluent 2>
  10 mM Tris-HCl (pH 8), 0.1 mM EDTA, 0.5% sodium azide

TABLE 9

| <PCR reaction solution> | |
| --- | --- |
| Distilled water | 20.52 |
| 5% NaN$_3$ | 0.23 |
| 20% BSA | 0.5 |
| 50% Glycerol | 10 |

TABLE 9-continued

<PCR reaction solution>

| 10 × Gene Taq buffer * | 5 |
| --- | --- |
| 2.5 mM dNTPs | 4 |
| 5 µM probe for CYP2C9 | 2 |
| 100 µM CYP2C9 F1 primer | 0.5 |
| 100 µM CYP2C9 R1 primer | 0.25 |
| 5 µM probe for VKORC1 | 2 |
| 100 µM VKORC1 F2 primer | 0.5 |
| 100 µM VKORC1 R2 primer | 0.25 |
| 5 U/µl Gene Taq FP * | 0.25 |
| Total | 46 µL |

<Probes>

```
Probe for CYP2C9
                                  (SEQ ID NO: 45)
5'-ggagaaggtcaaGgtatc-(BODIPY FL)-3'

Probe for VKORC1 gene
                                  (SEQ ID NO: 62)
5'-aagGgtcgatgatctc-(PACIFIC BLUE)-3'
```

<Primer Set>

```
CYP2C9 F1 primer
                                  (SEQ ID NO: 5)
5'-gagccctgcatgcaa-3'

CYP2C9 R1 primer
                                  (SEQ ID NO: 18)
5'-gatactatgaatttggggacttcgaa-3'

VKORC1 gene F2 primer
                                  (SEQ ID NO: 29)
5'-gaggatagggtcagtgacatggaa-3'

VKORC1 gene R2 primer
                                  (SEQ ID NO: 38)
5'-ccctgcccgagaaaggtgat-3'
```

Figure 5:
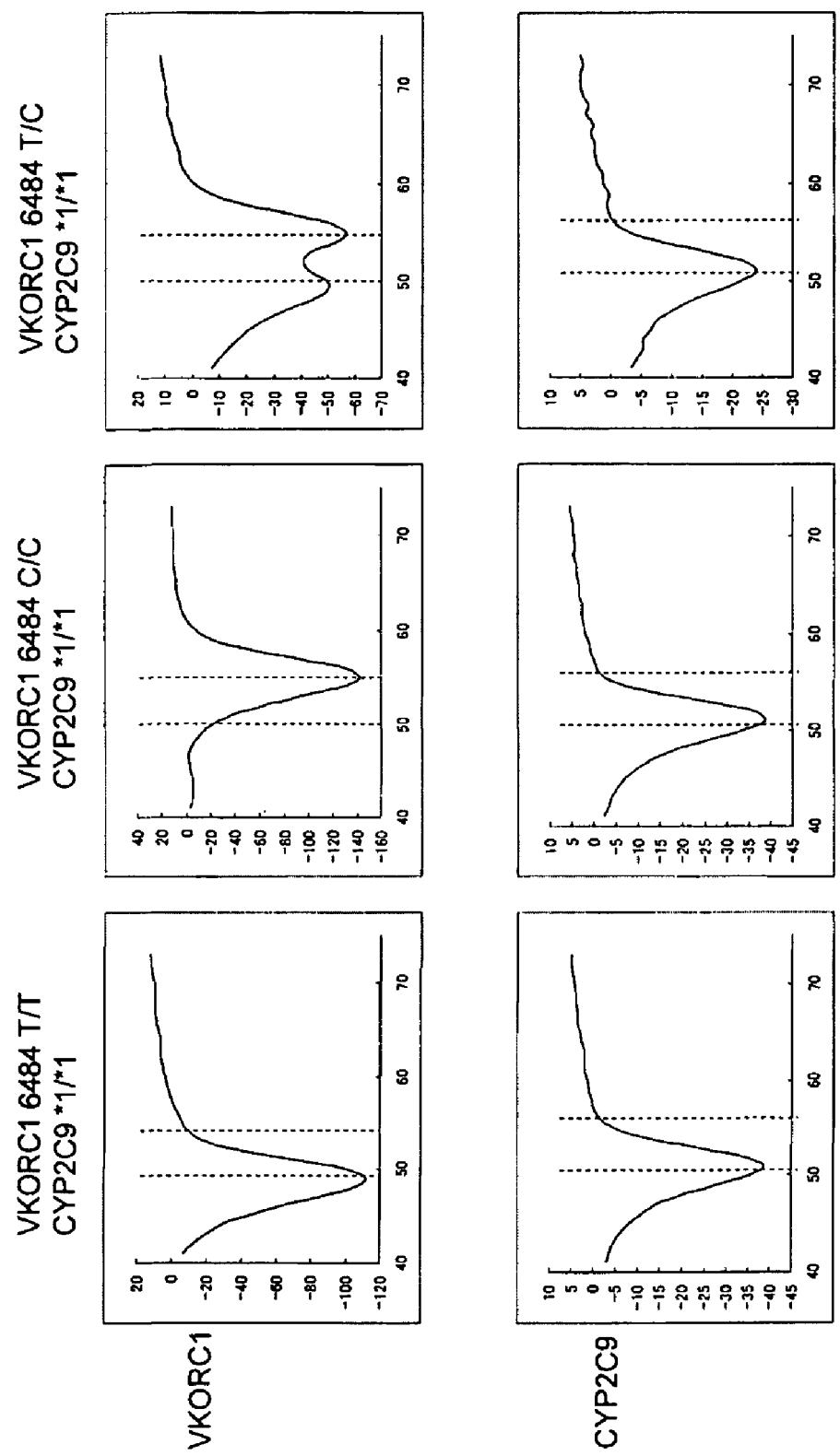
FIG. 5 shows graphs indicating the results of Tm analysis in a further example of the present invention.
Figure 6:
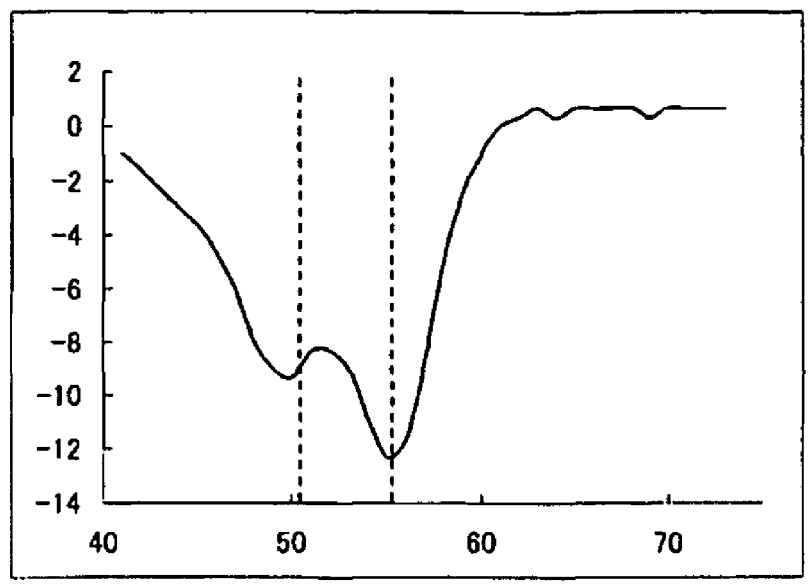
FIG. 6 shows graphs indicating the results of Tm analysis in still another example of the present invention.
Figure 6:
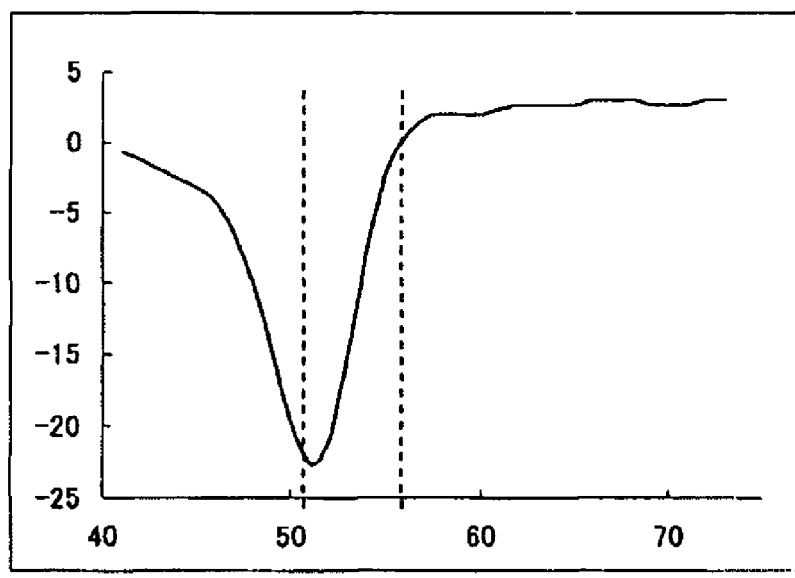

These results are shown in FIGS. 5 and 6. FIG. 5 shows the results obtained using the purified genome as a sample, while FIG. 6 shows the result obtained using blood as a sample. As shown in FIG. 5, the respective polymorphisms of the CYP2C9 genes and the VKORC1 genes in the respective samples were determined from the peaks of the signals. The results obtained from this example agreed with genomic information. Furthermore, as shown in FIG. 5, with respect to the VKORC1 genes that are homozygotes, 6484T/T and 6484C/C had peaks obtained at different positions. Accordingly, it was proved that base 6484 was able to be differentiated to be detected. Similarly with respect to the heterozygotes, two peaks corresponding to the aforementioned two homozygotes were obtained and thus it also was proved that both were able to be differentiated. Moreover, as shown in FIG. 6, similarly in the case of using the blood sample, it was proved, as in the case of using the purified genome, that the respective genes were amplified and the peaks corresponding to the respective polymorphisms were obtained. As described above, the use of a primer set of the present invention made it possible to amplify the CYP2C9 gene and the VKORC1 gene simultaneously in the same reaction solution and to analyze the respective polymorphisms of the genes using the same reaction solution.

INDUSTRIAL APPLICABILITY

As described above, the primer set of the present invention makes it possible to simultaneously and specifically amplify regions including sites where polymorphisms to be detected are generated in the CYP2C9 gene and the VKORC1 gene that are involved in the warfarin effect, respectively, in the same reaction solution. This allows time and cost to be reduced, which is different from the conventional methods described above. Furthermore, since the target regions of two genes can be amplified specifically in the same reaction solution as described above, the use of, for example, two types of probes complementary to the sequences to be subjected to detection in the respective target regions allows the Tm analysis to be performed by directly using the reaction solution to type each of the two types of polymorphisms. Moreover, since amplification and typing can be carried out using one reaction solution, the operation can be automated. The use of the primer set of the present invention allows a pretreatment to be omitted even in the case of, for example, a contaminated sample (for instance, whole blood or oral mucosa), and therefore the amplification reaction can be carried out quicker and more easily. Furthermore, when the primer set of the present invention is used, the amplification reaction can be carried out with higher amplification efficiency as compared to conventional cases and thus the amplification reaction time also can be shortened. Therefore, according to the primer set of the present invention, the reagent including the same, and the process for producing amplification products using them, since respective polymorphisms of the respective genes can be analyzed quickly and easily, it can be said that they are considerably effective in the medical field.

[Sequence Table]
TF08005-01.5T25.txt

The invention claimed is:

1. A primer set comprising primer sets (1) and (2):

Primer set (1):
 a primer set consisting of oligonucleotide (F1) and oligonucleotide (R1): (F1): an oligonucleotide consisting of the base sequence selected from any of SEQ ID NO: 3 to 7, and (R1): an oligonucleotide consisting of the base sequence selected from any of SEQ ID NO: 8 to 25, and Primer set (2):
 a primer set consisting of oligonucleotide (F2) oligonucleotide (R2): (F2): an oligonucleotide consisting of the base sequence selected from any of SEQ ID NO: 26 to 32, and (R2): an oligonucleotide consisting of the base sequence selected from any of SEQ ID NO: 33 to 40.

2. The primer set according to claim 1, wherein the primer sets (1) and (2) are the following primer sets (1') and (2'), respectively:

Primer set (1'):
 a primer set consisting of oligonucleotide (F1') and oligonucleotide (R1'): (F1'): an oligonucleotide consisting of SEQ ID NO: 5, and (R1'): an oligonucleotide consisting of the base sequence of SEQ ID NO: 18, and Primer set (2'):
 a primer set consisting of oligonucleotide (F2') and a reverse primer composed of the following oligonucleotide (R2'): (F2'): an oligonucleotide consisting of the base sequence of SEQ ID NO: 29, and (R2'): an oligonucleotide consisting of the base sequence of SEQ ID NO: 38.

3. A reagent composition comprising the primer set for gene amplification according to claim 1.

4. The reagent composition according to claim 3, further comprising fluorescently-labeled probes composed of oligonucleotides indicated in (P1) and (P2) below:

(P1): an oligonucleotide consisting of the base sequence of SEQ ID NO: 44 or oligonucleotide consisting of the base sequence of SEQ ID NO: 45, and (P2): an oligonucleotide consisting of the base sequence of SEQ ID NO: 51 or oligonucleotide consisting of the base sequence of SEQ ID NO: 62.

5. A process for producing amplification products of two types of genes by a gene amplification method,
 wherein the two types of genes are cytochrome P450 2C9 (CYP2C9 gene and vitamin K epoxide reductase complex subunit 1 (VKORC1) gene, and the process comprises the following process (I):
(I) amplifying the CYP2C9 gene and the VKORC1 gene simultaneously in the same reaction solution using a primer set for gene amplification according to claim 1, with nucleic acid contained in a sample being used as a template.

6. The process for producing amplification products according to claim 5, wherein at least one of a probe that hybridizes to a site to be detected in the CYP2C9 gene and a probe that hybridizes to a site to be detected in the VKORC1 gene further is added to the reaction solution in the process (I).

7. The process for producing amplification products according to claim 6, wherein the probe is at least one probe selected from the group consisting of oligonucleotides indicated in (P1) and (P2) below:
(P1) oligonucleotide consisting of the base sequence of SEQ ID NO: 44 and oligonucleotide consisting of the base sequence of SEQ ID NO: 45, and
(P2) oligonucleotide consisting of the base sequence of SEQ ID NO: 51 and oligonucleotide consisting of the base sequence of SEQ ID NO: 62.

8. The process for producing amplification products according to claim 6, wherein the probe is a fluorescently-labeled probe.

9. The process for producing amplification products according to claim 8, wherein the process further comprises the following process (II):
(II) measuring fluorescence intensity of a fluorescent label in the fluorescently-labeled probe in the reaction solution.

10. The process for producing amplification products according to claim 5, wherein the sample is a biological sample.

11. The process for producing amplification products according to claim 10, wherein the biological sample is whole blood.

12. The process for producing amplification products according to claim 11, wherein the ratio of the whole blood sample to be added to the reaction solution is 0.1 to 0.5 vol %.

13. A polymorphism analysis method of analyzing polymorphisms of sites to be detected in genes,
wherein the genes are the CYP2C9 gene and the VKORC1 gene, and
the method comprises the following processes (i) to (iv):
(i) simultaneously amplifying a region including a site to be detected in the CYP2C9 gene and a region including a site to be detected in the VKORC1 gene in the same reaction solution by a process for producing amplification products according to claim 5,
(ii) preparing a reaction solution that contains an amplification product of the CYP2C9 gene and an amplification product of the VKORC1 gene obtained in process (i) as well as probes capable of hybridizing to the respective sites to be detected in the respective genes,
(iii) measuring signal values that indicate melting states of respective hybridization products between the respective amplification products and the respective probes while changing temperature of the reaction solution, and
(iv) determining polymorphisms of the respective sites to be detected from a change in the signal values accompanying a change in the temperature.

14. The polymorphism analysis method according to claim 13, wherein in the process (i), probes capable of hybridizing to the respective sites to be detected are added to the reaction solution prior to an amplification reaction.

15. The primer set according to claim 1, wherein the oligonucleotide (F1) consists of the base sequence selected from any of SEQ ID NO: 3 to 5, the oligonucleotide (R1) consists of the base sequence selected from any of SEQ ID NO: 15 to 18, the oligonucleotide (F2) consists of the base sequence selected from any of SEQ ID NO: 26 to 29, and the oligonucleotide (R2) consists of the base sequence selected from any of SEQ ID NO: 33 to 38.

* * * * *

SEQUENCE LISTING

```
<160> NUMBER OF SEQ ID NOS: 53

<210> SEQ ID NO 1
<211> LENGTH: 1000
<212> TYPE: DNA
<213> ORGANISM: Homo sapiens

<400> SEQUENCE: 1
tccatccagg tcagtaacag gtcagtatgt cttttgattg gagattttat tccatttaca      60
ttcagtgtta ttattgataa gtaaggactt acccatgccc ctttgttatt tgttttctgg     120
ttgttttgtg gacttctctt ccttctttca tttcttcctg tcttcctttta ttgaagagaa    180
```

-continued

| | |
|---|---|
| ttttctccac ttatatgtgt acagattttt cttaatatct ggtttatggc agttacacat | 240 |
| ttgtgcatct gtaaccatcc tctcttaag tttgcatata cttccagcac tataatttaa | 300 |
| atttataatg atgtttggat accttcatga ttcatatacc cctgaattgc tacaacaaat | 360 |
| gtgccatttt tctccttttc catcagtttt tacttgtgtc ttatcagcta aagtccagga | 420 |
| agagattgaa cgtgtgattg cagaaaccg agcccctgc atgcaagaca ggagccacat | 480 |
| gccctacaca gatgctgtgg tgcacgaggt ccagagatac attgaccttc tccccaccag | 540 |
| cctgccccat gcagtgacct gtgacattaa attcagaaac tatctcattc ccaaggtaag | 600 |
| tttgtttctc ctacactgca actccatgtt ttcgaagtcc ccaaattcat agtatcattt | 660 |
| ttaaacctct accatcaccg ggtgagagaa gtgcataact catatgtatg cagtttaac | 720 |
| tggacttct cttgtttcca gtttggggct ataaaggttt gtaacaggtc ctagtgtctg | 780 |
| gcagtgtgtg ttctccagat ttattatctt tcttcaagat tggtttggct actcttaggt | 840 |
| gcttatattt ccaaataatt tttaaaggta ttagtttgtc aatttcccaa aaccttgggc | 900 |
| tggaatttct ggcagggtga cactaaattt ataggctagt ttggaaagaa ctgaatcttg | 960 |
| acacgttgag gctttccatt cctgaatata attatgcttc | 1000 |

<210> SEQ ID NO 2
<211> LENGTH: 1000
<212> TYPE: DNA
<213> ORGANISM: Homo sapiens

<400> SEQUENCE: 2

| | |
|---|---|
| cgttatacca gccttgccat tttaagaatt acttaagggc cgggcgcggt ggcccactcc | 60 |
| tgtaatccca gcactttggg aggccgaggc ggatggatca cttgaagtca ggagttgacc | 120 |
| agcctggcca acatggtgaa agcctgtctc taccaaaaat agaaaaatta atcgggcgct | 180 |
| atggcgggtg ccttaatccc agctactcgg gggggctaag gcaggagaat cgcttgaacc | 240 |
| cgggaggcgg aggtttcagt gagccgagat cgcgccactg cactccagcc tgggccagag | 300 |
| tgagactccg tctcaaaaaa aaaaaaaaaa aaaaaaaaa agagacttac ttaaggtcta | 360 |
| agatgaaaag caggggcctac ggagtagcca cgtccgggcc tggtctgggg agaggggagg | 420 |
| atagggtcag tgacatggaa tcctgacgtg gccaaaggtg cccggtgcca ggagatcatc | 480 |
| gacccttgga ctaggatggg aggtcgggga acagaggata gcccaggtgg cttcttggaa | 540 |
| atcacctttc tcgggcaggg tccaaggcac tgggttgaca gtcctaacct ggttccaccc | 600 |
| caccccaccc ctctgccagg tggggcaggg gtttcgggct ggtggagcat gtgctgggac | 660 |
| aggacagcat cctcaatcaa tccaacagca tattcggttg catcttctac acactacagc | 720 |
| tattgttagg tgagtggctc cgccccctcc ctgcccgccc cgccccgccc ctcatccccc | 780 |
| ttggtcagct cagccccact ccatgcaatc ttggtgatcc acacagctga cagccagcta | 840 |
| gctgctcatc acgagcgtc ctgcgggtgg ggatgtgggg aggtaactaa caggagtctt | 900 |
| ttaattggtt taagtactgt tagaggctga agggcctta aagacatcct aggtcccag | 960 |
| gttttttgtt tgttgttgtt ttgagacagg gtctggctct | 1000 |

<210> SEQ ID NO 3
<211> LENGTH: 18
<212> TYPE: DNA
<213> ORGANISM: Artificial
<220> FEATURE:
<223> OTHER INFORMATION: forward primer

<400> SEQUENCE: 3
cggagcccct gcatgcaa                                                    18

<210> SEQ ID NO 4
<211> LENGTH: 17
<212> TYPE: DNA
<213> ORGANISM: Artificial
<220> FEATURE:
<223> OTHER INFORMATION: forward primer

<400> SEQUENCE: 4
ggagcccctg catgcaa                                                     17

<210> SEQ ID NO 5
<211> LENGTH: 16
<212> TYPE: DNA
<213> ORGANISM: Artificial
<220> FEATURE:
<223> OTHER INFORMATION: forward primer

<400> SEQUENCE: 5
gagcccctgc atgcaa                                                      16

<210> SEQ ID NO 6
<211> LENGTH: 15
<212> TYPE: DNA
<213> ORGANISM: Artificial
<220> FEATURE:
<223> OTHER INFORMATION: forward primer

<400> SEQUENCE: 6
agcccctgca tgcaa                                                       15

<210> SEQ ID NO 7
<211> LENGTH: 14
<212> TYPE: DNA
<213> ORGANISM: Artificial
<220> FEATURE:
<223> OTHER INFORMATION: forward primer

<400> SEQUENCE: 7
gcccctgcat gcaa                                                        14

<210> SEQ ID NO 8
<211> LENGTH: 36
<212> TYPE: DNA
<213> ORGANISM: Artificial
<220> FEATURE:
<223> OTHER INFORMATION: reverse primer

<400> SEQUENCE: 8
gtttaaaaat gatactatga atttggggac ttcgaa                                36

<210> SEQ ID NO 9
<211> LENGTH: 35
<212> TYPE: DNA
<213> ORGANISM: Artificial
<220> FEATURE:
<223> OTHER INFORMATION: reverse primer

<400> SEQUENCE: 9
tttaaaaatg atactatgaa tttggggact tcgaa                                 35

<210> SEQ ID NO 10
<211> LENGTH: 34
<212> TYPE: DNA
<213> ORGANISM: Artificial
<220> FEATURE:

<223> OTHER INFORMATION: reverse primer

<400> SEQUENCE: 10
ttaaaaatga tactatgaat ttggggactt cgaa                                    34

<210> SEQ ID NO 11
<211> LENGTH: 33
<212> TYPE: DNA
<213> ORGANISM: Artificial
<220> FEATURE:
<223> OTHER INFORMATION: reverse primer

<400> SEQUENCE: 11
taaaaatgat actatgaatt tggggacttc gaa                                     33

<210> SEQ ID NO 12
<211> LENGTH: 32
<212> TYPE: DNA
<213> ORGANISM: Artificial
<220> FEATURE:
<223> OTHER INFORMATION: reverse primer

<400> SEQUENCE: 12
aaaaatgata ctatgaattt ggggacttcg aa                                      32

<210> SEQ ID NO 13
<211> LENGTH: 31
<212> TYPE: DNA
<213> ORGANISM: Artificial
<220> FEATURE:
<223> OTHER INFORMATION: reverse primer

<400> SEQUENCE: 13
aaaatgatac tatgaatttg gggacttcga a                                       31

<210> SEQ ID NO 14
<211> LENGTH: 30
<212> TYPE: DNA
<213> ORGANISM: Artificial
<220> FEATURE:
<223> OTHER INFORMATION: reverse primer

<400> SEQUENCE: 14
aaatgatact atgaatttgg ggacttcgaa                                         30

<210> SEQ ID NO 15
<211> LENGTH: 29
<212> TYPE: DNA
<213> ORGANISM: Artificial
<220> FEATURE:
<223> OTHER INFORMATION: reverse primer

<400> SEQUENCE: 15
aatgatacta tgaatttggg gacttcgaa                                          29

<210> SEQ ID NO 16
<211> LENGTH: 28
<212> TYPE: DNA
<213> ORGANISM: Artificial
<220> FEATURE:
<223> OTHER INFORMATION: reverse primer

<400> SEQUENCE: 16
atgatactat gaatttgggg acttcgaa                                           28

<210> SEQ ID NO 17

```
<211> LENGTH: 27
<212> TYPE: DNA
<213> ORGANISM: Artificial
<220> FEATURE:
<223> OTHER INFORMATION: reverse primer

<400> SEQUENCE: 17
tgatactatg aatttgggga cttcgaa                                              27

<210> SEQ ID NO 18
<211> LENGTH: 26
<212> TYPE: DNA
<213> ORGANISM: Artificial
<220> FEATURE:
<223> OTHER INFORMATION: reverse primer

<400> SEQUENCE: 18
gatactatga atttggggac ttcgaa                                               26

<210> SEQ ID NO 19
<211> LENGTH: 25
<212> TYPE: DNA
<213> ORGANISM: Artificial
<220> FEATURE:
<223> OTHER INFORMATION: reverse primer

<400> SEQUENCE: 19
atactatgaa tttggggact tcgaa                                                25

<210> SEQ ID NO 20
<211> LENGTH: 24
<212> TYPE: DNA
<213> ORGANISM: Artificial
<220> FEATURE:
<223> OTHER INFORMATION: reverse primer

<400> SEQUENCE: 20
tactatgaat ttggggactt cgaa                                                 24

<210> SEQ ID NO 21
<211> LENGTH: 23
<212> TYPE: DNA
<213> ORGANISM: Artificial
<220> FEATURE:
<223> OTHER INFORMATION: reverse primer

<400> SEQUENCE: 21
actatgaatt tggggacttc gaa                                                  23

<210> SEQ ID NO 22
<211> LENGTH: 22
<212> TYPE: DNA
<213> ORGANISM: Artificial
<220> FEATURE:
<223> OTHER INFORMATION: reverse primer

<400> SEQUENCE: 22
ctatgaattt ggggacttcg aa                                                   22

<210> SEQ ID NO 23
<211> LENGTH: 21
<212> TYPE: DNA
<213> ORGANISM: Artificial
<220> FEATURE:
<223> OTHER INFORMATION: reverse primer

<400> SEQUENCE: 23
```

```
tatgaatttg gggacttcga a                                                  21

<210> SEQ ID NO 24
<211> LENGTH: 20
<212> TYPE: DNA
<213> ORGANISM: Artificial
<220> FEATURE:
<223> OTHER INFORMATION: reverse primer

<400> SEQUENCE: 24
atgaatttgg ggacttcgaa                                                    20

<210> SEQ ID NO 25
<211> LENGTH: 19
<212> TYPE: DNA
<213> ORGANISM: Artificial
<220> FEATURE:
<223> OTHER INFORMATION: reverse primer

<400> SEQUENCE: 25
tgaatttggg gacttcgaa                                                     19

<210> SEQ ID NO 26
<211> LENGTH: 27
<212> TYPE: DNA
<213> ORGANISM: Artificial
<220> FEATURE:
<223> OTHER INFORMATION: forward primer

<400> SEQUENCE: 26
ggggaggata gggtcagtga catggaa                                            27

<210> SEQ ID NO 27
<211> LENGTH: 26
<212> TYPE: DNA
<213> ORGANISM: Artificial
<220> FEATURE:
<223> OTHER INFORMATION: forward primer

<400> SEQUENCE: 27
gggaggatag ggtcagtgac atggaa                                             26

<210> SEQ ID NO 28
<211> LENGTH: 25
<212> TYPE: DNA
<213> ORGANISM: Artificial
<220> FEATURE:
<223> OTHER INFORMATION: forward primer

<400> SEQUENCE: 28
ggaggatagg gtcagtgaca tggaa                                              25

<210> SEQ ID NO 29
<211> LENGTH: 24
<212> TYPE: DNA
<213> ORGANISM: Artificial
<220> FEATURE:
<223> OTHER INFORMATION: forward primer

<400> SEQUENCE: 29 gaggatagggtcagtgacat ggaa                                                24

<210> SEQ ID NO 30
<211> LENGTH: 23
<212> TYPE: DNA
<213> ORGANISM: Artificial
<220> FEATURE:
```

```
<223> OTHER INFORMATION: forward primer

<400> SEQUENCE: 30
aggatagggt cagtgacatg gaa                                        23

<210> SEQ ID NO 31
<211> LENGTH: 22
<212> TYPE: DNA
<213> ORGANISM: Artificial
<220> FEATURE:
<223> OTHER INFORMATION: forward primer

<400> SEQUENCE: 31
ggatagggtc agtgacatgg aa                                         22

<210> SEQ ID NO 32
<211> LENGTH: 21
<212> TYPE: DNA
<213> ORGANISM: Artificial
<220> FEATURE:
<223> OTHER INFORMATION: forward primer

<400> SEQUENCE: 32
gatagggtca gtgacatgga a                                          21

<210> SEQ ID NO 33
<211> LENGTH: 25
<212> TYPE: DNA
<213> ORGANISM: Artificial
<220> FEATURE:
<223> OTHER INFORMATION: reverse primer

<400> SEQUENCE: 33
ttggaccctg cccgagaaag gtgat                                      25

<210> SEQ ID NO 34
<211> LENGTH: 24
<212> TYPE: DNA
<213> ORGANISM: Artificial
<220> FEATURE:
<223> OTHER INFORMATION: reverse primer

<400> SEQUENCE: 34
tggaccctgc ccgagaaagg tgat                                       24

<210> SEQ ID NO 35
<211> LENGTH: 23
<212> TYPE: DNA
<213> ORGANISM: Artificial
<220> FEATURE:
<223> OTHER INFORMATION: reverse primer

<400> SEQUENCE: 35
ggaccctgcc cgagaaaggt gat                                        23

<210> SEQ ID NO 36
<211> LENGTH: 22
<212> TYPE: DNA
<213> ORGANISM: Artificial
<220> FEATURE:
<223> OTHER INFORMATION: reverse primer

<400> SEQUENCE: 36
gaccctgccc gagaaaggtg at                                         22

<210> SEQ ID NO 37
```

-continued

```
<211> LENGTH: 21
<212> TYPE: DNA
<213> ORGANISM: Artificial
<220> FEATURE:
<223> OTHER INFORMATION: reverse primer

<400> SEQUENCE: 37
accctgcccg agaaaggtga t                                              21

<210> SEQ ID NO 38
<211> LENGTH: 20
<212> TYPE: DNA
<213> ORGANISM: Artificial
<220> FEATURE:
<223> OTHER INFORMATION: reverse primer

<400> SEQUENCE: 38
ccctgcccga gaaaggtgat                                                20

<210> SEQ ID NO 39
<211> LENGTH: 19
<212> TYPE: DNA
<213> ORGANISM: Artificial
<220> FEATURE:
<223> OTHER INFORMATION: reverse primer

<400> SEQUENCE: 39
cctgcccgag aaaggtgat                                                 19

<210> SEQ ID NO 40
<211> LENGTH: 18
<212> TYPE: DNA
<213> ORGANISM: Artificial
<220> FEATURE:
<223> OTHER INFORMATION: reverse primer

<400> SEQUENCE: 40
ctgcccgaga aaggtgat                                                  18

<210> SEQ ID NO 41
<211> LENGTH: 22
<212> TYPE: DNA
<213> ORGANISM: Artificial
<220> FEATURE:
<223> OTHER INFORMATION: probe

<400> SEQUENCE: 41
gtggggagaa ggtcaaggta tc                                             22

<210> SEQ ID NO 42
<211> LENGTH: 21
<212> TYPE: DNA
<213> ORGANISM: Artificial
<220> FEATURE:
<223> OTHER INFORMATION: probe

<400> SEQUENCE: 42
tggggagaag gtcaaggtat c                                              21

<210> SEQ ID NO 43
<211> LENGTH: 20
<212> TYPE: DNA
<213> ORGANISM: Artificial
<220> FEATURE:
<223> OTHER INFORMATION: probe

<400> SEQUENCE: 43
```
ggggagaagg tcaaggtatc                               20

<210> SEQ ID NO 44
<211> LENGTH: 19
<212> TYPE: DNA
<213> ORGANISM: Artificial
<220> FEATURE:
<223> OTHER INFORMATION: probe

<400> SEQUENCE: 44
gggagaaggt caaggtatc                                19

<210> SEQ ID NO 45
<211> LENGTH: 18
<212> TYPE: DNA
<213> ORGANISM: Artificial
<220> FEATURE:
<223> OTHER INFORMATION: probe

<400> SEQUENCE: 45
ggagaaggtc aaggtatc                                 18

<210> SEQ ID NO 46
<211> LENGTH: 17
<212> TYPE: DNA
<213> ORGANISM: Artificial
<220> FEATURE:
<223> OTHER INFORMATION: probe

<400> SEQUENCE: 46
gagaaggtca aggtatc                                  17

<210> SEQ ID NO 47
<211> LENGTH: 24
<212> TYPE: DNA
<213> ORGANISM: Artificial
<220> FEATURE:
<223> OTHER INFORMATION: probe2-1

<400> SEQUENCE: 47
catcgaccct tggactagga tggg                          24

<210> SEQ ID NO 48
<211> LENGTH: 23
<212> TYPE: DNA
<213> ORGANISM: Artificial
<220> FEATURE:
<223> OTHER INFORMATION: probe

<400> SEQUENCE: 48
catcgaccct tggactagga tgg                           23

<210> SEQ ID NO 49
<211> LENGTH: 22
<212> TYPE: DNA
<213> ORGANISM: Artificial
<220> FEATURE:
<223> OTHER INFORMATION: probe

<400> SEQUENCE: 49
catcgaccct tggactagga tg                            22

```
<210> SEQ ID NO 50
<211> LENGTH: 21
<212> TYPE: DNA
<213> ORGANISM: Artificial
<220> FEATURE:
<223> OTHER INFORMATION: probe

<400> SEQUENCE: 50
catcgaccct tggactagga t                                              21

<210> SEQ ID NO 51
<211> LENGTH: 20
<212> TYPE: DNA
<213> ORGANISM: Artificial
<220> FEATURE:
<223> OTHER INFORMATION: probe

<400> SEQUENCE: 51
catcgaccct tggactagga                                                20

<210> SEQ ID NO 52
<211> LENGTH: 19
<212> TYPE: DNA
<213> ORGANISM: Artificial
<220> FEATURE:
<223> OTHER INFORMATION: probe

<400> SEQUENCE: 52
catcgaccct tggactagg                                                 19

<210> SEQ ID NO 53
<211> LENGTH: 18
<212> TYPE: DNA
<213> ORGANISM: Artificial
<220> FEATURE:
<223> OTHER INFORMATION: probe

<400> SEQUENCE: 53
catcgaccct tggactag                                                  18
```